United States Patent
Al-Ali et al.

(10) Patent No.: US 8,781,544 B2
(45) Date of Patent: Jul. 15, 2014

(54) MULTIPLE WAVELENGTH OPTICAL SENSOR

(75) Inventors: Ammar Al-Ali, Tustin, CA (US);
Mohamed K. Diab, Ladera Ranch, CA (US); Arun Panch, Mission Viejo, CA (US); Yassir Abdul-Hafiz, Irvine, CA (US); William Jack MacNeish, III, Costa Mesa, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 1444 days.

(21) Appl. No.: 12/056,179

(22) Filed: Mar. 26, 2008

(65) Prior Publication Data

US 2008/0242958 A1    Oct. 2, 2008

Related U.S. Application Data

(60) Provisional application No. 60/920,474, filed on Mar. 27, 2007, provisional application No. 60/923,630, filed on Apr. 14, 2007, provisional application No. 61/033,007, filed on Mar. 2, 2008.

(51) Int. Cl.
*A61B 5/00*    (2006.01)

(52) U.S. Cl.
USPC .......................................... 600/323; 600/310

(58) Field of Classification Search
USPC ................................................ 600/323, 310
See application file for complete search history.

(56) References Cited

U.S. PATENT DOCUMENTS

| | | |
|---|---|---|
| 3,910,701 A | 10/1975 | Henderson et al. |
| 3,998,550 A | 12/1976 | Konishi et al. |
| 4,014,321 A | 3/1977 | March |
| 4,157,708 A | 6/1979 | Imura |
| 4,167,331 A | 9/1979 | Nielsen |
| 4,266,554 A | 5/1981 | Hamaguri |
| 4,267,844 A | 5/1981 | Yamanishi |
| 4,446,871 A | 5/1984 | Imura |
| 4,531,527 A | 7/1985 | Reinhold, Jr. et al. |
| 4,586,513 A | 5/1986 | Hamaguri |
| 4,621,643 A | 11/1986 | New et al. |

(Continued)

FOREIGN PATENT DOCUMENTS

| | | |
|---|---|---|
| EP | 0 41 92 23 | 3/1991 |
| EP | 0 569 670 | 11/1993 |

(Continued)

OTHER PUBLICATIONS

PCT Search Report of International Application No. PCT/US2008/058327, Mailing Date of Aug. 12, 2008, in 6 pp.

(Continued)

*Primary Examiner* — Max Hindenburg
*Assistant Examiner* — Renee Danega
(74) *Attorney, Agent, or Firm* — Knobbe Martens Olson & Bear LLP

(57) ABSTRACT

A multiple wavelength optical sensor has an emitter configured to radiate light having a plurality of wavelengths into a tissue site. The emitter comprises a plurality of LEDs configured in an array and connected within an electrical grid. A detector is configured to receive the light after absorption by pulsatile blood flow within the tissue site. The detector generates a sensor signal capable of being processed by a patient monitor so as to derive oxygen saturation, carboxyhemoglobin, methemoglobin and total hemoglobin.

21 Claims, 32 Drawing Sheets

(56) References Cited

U.S. PATENT DOCUMENTS

| | | | |
|---|---|---|---|
| 4,653,498 A | 3/1987 | New, Jr. et al. |
| 4,655,225 A | 4/1987 | Dahne et al. |
| 4,685,464 A | 8/1987 | Goldberger et al. |
| 4,694,833 A | 9/1987 | Hamaguri |
| 4,695,955 A | 9/1987 | Faisandier |
| 4,700,708 A | 10/1987 | New et al. |
| 4,714,341 A | 12/1987 | Hamaguri et al. |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,805,623 A | 2/1989 | Jobsis |
| 4,832,484 A | 5/1989 | Aoyagi et al. |
| 4,846,183 A | 7/1989 | Martin |
| 4,854,328 A | 8/1989 | Pollack |
| 4,863,265 A | 9/1989 | Flower et al. |
| 4,867,557 A | 9/1989 | Takatani et al. |
| 4,867,571 A | 9/1989 | Frick et al. |
| 4,869,254 A | 9/1989 | Stone et al. |
| 4,907,876 A | 3/1990 | Suzuki et al. |
| 4,911,167 A | 3/1990 | Corenman et al. |
| 4,934,372 A | 6/1990 | Corenman et al. |
| 4,938,218 A | 7/1990 | Goodman et al. |
| 4,942,877 A | 7/1990 | Sakai et al. |
| 4,955,379 A | 9/1990 | Hall |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,986,665 A | 1/1991 | Yamanishi et al. |
| 4,997,769 A | 3/1991 | Lundsgaard |
| 5,025,791 A | 6/1991 | Niwa |
| RE33,643 E | 7/1991 | Isaacson et al. |
| 5,028,787 A | 7/1991 | Rosenthal et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle |
| 5,069,213 A | 12/1991 | Polczynski |
| 5,077,476 A | 12/1991 | Rosenthal |
| 5,078,136 A | 1/1992 | Stone et al. |
| 5,137,023 A | 8/1992 | Mendelson et al. |
| 5,163,438 A | 11/1992 | Gordon et al. |
| 5,189,609 A | 2/1993 | Tivig et al. |
| 5,190,040 A | 3/1993 | Aoyagi |
| 5,209,230 A | 5/1993 | Swedlow et al. |
| 5,226,053 A | 7/1993 | Cho et al. |
| 5,246,002 A | 9/1993 | Prosser |
| 5,247,931 A | 9/1993 | Norwood |
| 5,259,381 A | 11/1993 | Cheung et al. |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,331,549 A | 7/1994 | Crawford, Jr. |
| 5,335,659 A | 8/1994 | Pologe et al. |
| 5,337,744 A | 8/1994 | Branigan |
| 5,337,745 A | 8/1994 | Benaron |
| 5,341,805 A | 8/1994 | Stavridi et al. |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,377,676 A | 1/1995 | Vari et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| D359,546 S | 6/1995 | Savage et al. |
| 5,421,329 A | 6/1995 | Casciani et al. |
| 5,424,545 A | 6/1995 | Block et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| RE35,122 E | 12/1995 | Corenman et al. |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,551,423 A | 9/1996 | Sugiura |
| 5,553,615 A | 9/1996 | Carim et al. |
| 5,555,882 A | 9/1996 | Richardson et al. |
| 5,561,275 A | 10/1996 | Savage et al. |
| 5,562,002 A | 10/1996 | Lalin |
| 5,575,284 A | 11/1996 | Athan et al. |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,713,355 A | 2/1998 | Richardson et al. |
| 5,719,589 A | 2/1998 | Norman et al. |
| 5,720,284 A | 2/1998 | Aoyagi et al. |
| D393,830 S | 4/1998 | Tobler et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |
| 5,782,237 A | 7/1998 | Casciani et al. |
| 5,782,756 A | 7/1998 | Mannheimer |
| 5,782,757 A * | 7/1998 | Diab et al. ............ 600/323 |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |

(56) References Cited

U.S. PATENT DOCUMENTS

| | | |
|---|---|---|
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,010 A | 10/1998 | Hibl |
| 5,818,985 A | 10/1998 | Merchant et al. |
| 5,823,950 A | 10/1998 | Diab et al. |
| 5,823,952 A | 10/1998 | Levinson et al. |
| 5,827,182 A | 10/1998 | Raley et al. |
| 5,830,131 A | 11/1998 | Caro et al. |
| 5,830,137 A | 11/1998 | Scharf |
| 5,833,618 A | 11/1998 | Caro et al. |
| 5,839,439 A | 11/1998 | Nierlich et al. |
| RE36,000 E | 12/1998 | Swedlow et al. |
| 5,842,979 A | 12/1998 | Jarman |
| 5,851,178 A | 12/1998 | Aronow |
| 5,851,179 A | 12/1998 | Ritson et al. |
| 5,853,364 A | 12/1998 | Baker, Jr. et al. |
| 5,857,462 A | 1/1999 | Thomas et al. |
| 5,860,919 A | 1/1999 | Kiani-Azarbayjany et al. |
| 5,865,736 A | 2/1999 | Baker, Jr. et al. |
| 5,876,348 A | 3/1999 | Sugo |
| 5,885,213 A | 3/1999 | Richardson et al. |
| 5,890,929 A | 4/1999 | Mills et al. |
| 5,891,022 A | 4/1999 | Pologe |
| 5,891,024 A | 4/1999 | Jarman et al. |
| 5,904,654 A | 5/1999 | Wohltmann et al. |
| 5,910,108 A | 6/1999 | Solenberger |
| 5,916,154 A | 6/1999 | Hobbs et al. |
| 5,919,133 A | 7/1999 | Taylor |
| 5,919,134 A | 7/1999 | Diab |
| 5,921,921 A | 7/1999 | Potratz et al. |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling |
| 5,978,691 A | 11/1999 | Mills |
| 5,983,122 A | 11/1999 | Jarman et al. |
| 5,995,855 A | 11/1999 | Kiani et al. |
| 5,995,856 A | 11/1999 | Mannheimer et al. |
| 5,995,859 A | 11/1999 | Takahashi |
| 5,997,343 A | 12/1999 | Mills et al. |
| 5,999,841 A | 12/1999 | Aoyagi et al. |
| 6,002,952 A | 12/1999 | Diab et al. |
| 6,006,119 A | 12/1999 | Soller et al. |
| 6,011,986 A | 1/2000 | Diab et al. |
| 6,014,576 A | 1/2000 | Raley |
| 6,018,673 A | 1/2000 | Chin et al. |
| 6,018,674 A | 1/2000 | Aronow |
| 6,023,541 A | 2/2000 | Merchant et al. |
| 6,027,452 A | 2/2000 | Flaherty et al. |
| 6,036,642 A | 3/2000 | Diab et al. |
| 6,045,509 A | 4/2000 | Caro et al. |
| 6,064,898 A | 5/2000 | Aldrich |
| 6,067,462 A | 5/2000 | Diab et al. |
| 6,068,594 A | 5/2000 | Schloemer et al. |
| 6,073,037 A | 6/2000 | Alam et al. |
| 6,081,735 A | 6/2000 | Diab et al. |
| 6,083,172 A | 7/2000 | Baker, Jr. et al. |
| 6,088,607 A | 7/2000 | Diab et al. |
| 6,094,592 A | 7/2000 | Yorkey et al. |
| 6,104,938 A | 8/2000 | Huiku |
| 6,110,522 A | 8/2000 | Lepper, Jr. et al. |
| 6,112,107 A | 8/2000 | Hannula |
| 6,122,042 A | 9/2000 | Wunderman et al. |
| 6,124,597 A | 9/2000 | Shehada |
| 6,144,868 A | 11/2000 | Parker |
| 6,149,588 A | 11/2000 | Noda et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,041 A | 12/2000 | Thomas et al. |
| 6,157,850 A | 12/2000 | Diab et al. |
| 6,165,005 A | 12/2000 | Mills et al. |
| 6,174,283 B1 | 1/2001 | Nevo et al. |
| 6,184,521 B1 | 2/2001 | Coffin, IV et al. |
| 6,192,261 B1 | 2/2001 | Gratton et al. |
| 6,206,830 B1 | 3/2001 | Diab et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,262,698 B1 | 7/2001 | Blum |
| 6,263,222 B1 | 7/2001 | Diab et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,304,675 B1 | 10/2001 | Osbourn et al. |
| 6,304,767 B1 | 10/2001 | Soller et al. |
| 6,321,100 B1 | 11/2001 | Parker |
| 6,330,468 B1 | 12/2001 | Scharf |
| 6,334,065 B1 | 12/2001 | Al-Ali et al. |
| 6,341,257 B1 | 1/2002 | Haaland |
| 6,343,224 B1 | 1/2002 | Parker |
| 6,349,228 B1 | 2/2002 | Kiani et al. |
| 6,351,658 B1 | 2/2002 | Middleman et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,363,269 B1 | 3/2002 | Hanna et al. |
| 6,368,283 B1 | 4/2002 | Xu et al. |
| 6,371,921 B1 | 4/2002 | Caro et al. |
| 6,374,129 B1 | 4/2002 | Chin et al. |
| 6,377,828 B1 | 4/2002 | Chaiken et al. |
| 6,377,829 B1 | 4/2002 | Al-Ali |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,408,198 B1 | 6/2002 | Hanna et al. |
| 6,411,833 B1 | 6/2002 | Baker, Jr. et al. |
| 6,415,166 B1 | 7/2002 | Van Hoy et al. |
| 6,415,233 B1 | 7/2002 | Haaland |
| 6,415,236 B2 | 7/2002 | Kobayashi et al. |
| 6,430,525 B1 | 8/2002 | Weber et al. |
| 6,434,408 B1 | 8/2002 | Heckel |
| 6,441,388 B1 | 8/2002 | Thomas et al. |
| 6,453,184 B1 | 9/2002 | Hyogo et al. |
| 6,455,340 B1 | 9/2002 | Chua et al. |
| 6,463,310 B1 | 10/2002 | Swedlow et al. |
| 6,463,311 B1 | 10/2002 | Diab |
| 6,466,824 B1 | 10/2002 | Struble |
| 6,470,199 B1 | 10/2002 | Kopotic et al. |
| 6,480,729 B2 | 11/2002 | Stone |
| 6,490,466 B1 | 12/2002 | Chew et al. |
| 6,497,659 B1 | 12/2002 | Rafert |
| 6,501,974 B2 | 12/2002 | Huiku |
| 6,501,975 B2 | 12/2002 | Diab et al. |
| 6,504,943 B1 | 1/2003 | Sweatt et al. |
| 6,505,059 B1 | 1/2003 | Kollias et al. |
| 6,505,060 B1 | 1/2003 | Norris |
| 6,505,061 B2 | 1/2003 | Larson |
| 6,505,133 B1 | 1/2003 | Hanna |
| 6,510,329 B2 | 1/2003 | Heckel |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,522,398 B2 | 2/2003 | Cadell et al. |
| 6,525,386 B1 | 2/2003 | Mills et al. |
| 6,526,300 B1 | 2/2003 | Kiani et al. |
| 6,526,301 B2 | 2/2003 | Larsen et al. |

(56) References Cited

U.S. PATENT DOCUMENTS

| | | |
|---|---|---|
| 6,528,809 B1 | 3/2003 | Thomas et al. |
| 6,537,225 B1 | 3/2003 | Mills |
| 6,541,756 B2 | 4/2003 | Schulz et al. |
| 6,542,763 B1 | 4/2003 | Yamashita et al. |
| 6,542,764 B1 | 4/2003 | Al-Ali et al. |
| 6,545,652 B1 | 4/2003 | Tsuji |
| 6,546,267 B1 | 4/2003 | Sugiura |
| 6,553,241 B2 | 4/2003 | Mannheimer et al. |
| 6,564,077 B2 | 5/2003 | Mortara |
| 6,571,113 B1 | 5/2003 | Fein et al. |
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,591,123 B2 | 7/2003 | Fein et al. |
| 6,594,511 B2 | 7/2003 | Stone et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B2 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Kianl et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali et al. |
| 6,675,106 B1 | 1/2004 | Keenan et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,690,466 B2 | 2/2004 | Miller et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,582 B2 | 4/2004 | Trepagnier et al. |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,728,560 B2 | 4/2004 | Kollias et al. |
| 6,735,459 B2 | 5/2004 | Parker |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,792,300 B1 | 9/2004 | Diab et al. |
| 6,800,373 B2 | 10/2004 | Corczyca |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,829,501 B2 | 12/2004 | Nielsen et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,861,641 B1 | 3/2005 | Adams |
| 6,869,402 B2 | 3/2005 | Arnold |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,917,422 B2 | 7/2005 | Samsoondar et al. |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B2 | 8/2005 | Kiani-Azarbayjany et al. |
| 6,931,269 B2 | 8/2005 | Terry |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,950,687 B2 | 9/2005 | Al-Ali |
| 6,956,572 B2 | 10/2005 | Zaleski |
| 6,961,598 B2 | 11/2005 | Diab |
| 6,970,792 B1 | 11/2005 | Diab |
| 6,975,891 B2 | 12/2005 | Pawluczyk |
| 6,979,812 B2 | 12/2005 | Al-Ali |
| 6,985,764 B2 | 1/2006 | Mason et al. |
| 6,987,994 B1 | 1/2006 | Mortz |
| 6,993,371 B2 | 1/2006 | Kiani et al. |
| 6,996,427 B2 | 2/2006 | Ali et al. |
| 6,999,904 B2 | 2/2006 | Weber et al. |
| 7,001,337 B2 | 2/2006 | Dekker |
| 7,003,338 B2 | 2/2006 | Weber et al. |
| 7,003,339 B2 | 2/2006 | Diab et al. |
| 7,006,856 B2 | 2/2006 | Baker, Jr. et al. |
| 7,015,451 B2 | 3/2006 | Dalke et al. |
| 7,024,233 B2 | 4/2006 | Ali et al. |

(56) References Cited

U.S. PATENT DOCUMENTS

| | | | |
|---|---|---|---|
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,080 B2 | 11/2007 | Acosta et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,729,733 B2 | 6/2010 | Al-Ali et al. |
| 7,734,320 B2 | 6/2010 | Al-Ali |
| 7,899,507 B2 | 3/2011 | Al-Ali et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |

(56) References Cited

U.S. PATENT DOCUMENTS

| | | |
|---|---|---|
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2001/0044700 A1 | 11/2001 | Kobayashi et al. |
| 2001/0045532 A1 | 11/2001 | Schulz et al. |
| 2002/0021269 A1 | 2/2002 | Rast |
| 2002/0026107 A1 | 2/2002 | Kiani et al. |
| 2002/0035318 A1 | 3/2002 | Mannheimer et al. |
| 2002/0038078 A1 | 3/2002 | Ito |
| 2002/0038081 A1 | 3/2002 | Fein et al. |
| 2002/0051290 A1 | 5/2002 | Hannington |
| 2002/0059047 A1 | 5/2002 | Haaland |
| 2002/0082488 A1 | 6/2002 | Al-Ali et al. |
| 2002/0095078 A1 | 7/2002 | Mannheimer et al. |
| 2002/0111748 A1 | 8/2002 | Kobayashi et al. |
| 2002/0115919 A1 | 8/2002 | Al-Ali |
| 2002/0154665 A1 | 10/2002 | Funabashi et al. |
| 2002/0156353 A1 | 10/2002 | Larson |
| 2002/0159002 A1 | 10/2002 | Chang |
| 2002/0161291 A1 | 10/2002 | Kianl et al. |
| 2002/0165440 A1 | 11/2002 | Mason et al. |
| 2002/0183819 A1 | 12/2002 | Struble |
| 2003/0045784 A1 | 3/2003 | Palatnik et al. |
| 2003/0045785 A1 | 3/2003 | Diab et al. |
| 2003/0049232 A1 | 3/2003 | Page et al. |
| 2003/0109775 A1 | 6/2003 | O'Neil et al. |
| 2003/0116769 A1* | 6/2003 | Song et al. ................ 257/79 |
| 2003/0117296 A1 | 6/2003 | Seely |
| 2003/0120160 A1 | 6/2003 | Yarita |
| 2003/0120164 A1 | 6/2003 | Nielsen et al. |
| 2003/0135099 A1 | 7/2003 | Al-Ali |
| 2003/0139657 A1 | 7/2003 | Solenberger |
| 2003/0160257 A1 | 8/2003 | Bader et al. |
| 2003/0195402 A1 | 10/2003 | Fein et al. |
| 2004/0006261 A1 | 1/2004 | Swedlow et al. |
| 2004/0033618 A1 | 2/2004 | Haass et al. |
| 2004/0034898 A1 | 2/2004 | Bruegl |
| 2004/0059209 A1 | 3/2004 | Al Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0133087 A1 | 7/2004 | Al Ali et al. |
| 2004/0138538 A1 | 7/2004 | Stetson |
| 2004/0138540 A1 | 7/2004 | Baker, Jr. et al. |
| 2004/0147822 A1 | 7/2004 | Al-Ali et al. |
| 2004/0147823 A1 | 7/2004 | Kiani et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167382 A1 | 8/2004 | Gardner et al. |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0229391 A1 | 11/2004 | Ohya et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0011488 A1 | 1/2005 | Doucet |
| 2005/0033128 A1 | 2/2005 | Al Ali et al. |
| 2005/0043902 A1 | 2/2005 | Haaland et al. |
| 2005/0049469 A1 | 3/2005 | Aoyagi et al. |
| 2005/0054908 A1 | 3/2005 | Blank et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085704 A1 | 4/2005 | Schulz et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker, Jr. et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0209515 A1 | 9/2005 | Hockersmith et al. |
| 2005/0228253 A1 | 10/2005 | Debreczeny |
| 2005/0250997 A1 | 11/2005 | Takedo et al. |
| 2006/0030764 A1 | 2/2006 | Porges et al. |
| 2006/0210120 A1 | 9/2006 | Rowe et al. |
| 2006/0211922 A1 | 9/2006 | Al-Ali et al. |
| 2006/0211923 A1* | 9/2006 | Al-Ali et al. ................ 600/310 |
| 2006/0211924 A1 | 9/2006 | Dalke et al. |
| 2006/0211925 A1 | 9/2006 | Lamego et al. |
| 2006/0211932 A1 | 9/2006 | Al-Ali et al. |
| 2006/0226992 A1 | 10/2006 | Al-Ali et al. |
| 2006/0229509 A1 | 10/2006 | Al-Ali et al. |
| 2006/0238358 A1 | 10/2006 | Al-Ali et al. |
| 2006/0241358 A1 | 10/2006 | Al-Ali et al. |
| 2006/0241363 A1 | 10/2006 | Al-Ali et al. |
| 2006/0264718 A1* | 11/2006 | Ruchti et al. ................ 600/310 |
| 2011/0009719 A1 | 1/2011 | Al-Ali et al. |
| 2011/0237914 A1 | 9/2011 | Lamego |

FOREIGN PATENT DOCUMENTS

| | | |
|---|---|---|
| EP | 0 675 541 | 10/1995 |
| EP | 1 080 683 | 3/2001 |
| EP | 1 895 892 | 5/2010 |
| EP | 2 305 104 | 4/2011 |
| JP | 61-28172 | 2/1986 |
| JP | 62-000324 | 1/1987 |
| JP | 63-275327 | 11/1988 |
| JP | 64-500495 | 2/1989 |
| JP | 2-145457 | 12/1990 |
| JP | 05-207993 | 8/1993 |
| JP | 6-505903 | 7/1994 |
| JP | 6-237013 | 8/1994 |
| JP | 7-281618 | 10/1995 |
| JP | 07-325546 | 12/1995 |
| JP | 9-192120 | 7/1997 |
| JP | H10-500026 | 1/1998 |
| JP | 10-216112 | 8/1998 |
| JP | 10-509352 | 9/1998 |
| JP | 10-269344 A | 10/1998 |
| JP | 10-295676 | 11/1998 |
| JP | 10-305026 | 11/1998 |
| JP | 11-163412 | 6/1999 |
| JP | 11-164826 | 6/1999 |
| JP | 11-506834 | 6/1999 |
| JP | 11-183377 | 7/1999 |
| JP | 2000-116625 | 4/2000 |
| JP | 2002-516689 | 6/2002 |
| JP | 2002-228579 | 8/2002 |
| JP | 2002-525151 | 8/2002 |
| JP | 2002-315739 | 10/2002 |
| JP | 2003-507718 | 2/2003 |
| JP | 2003084108 | 3/2003 |

(56) References Cited

FOREIGN PATENT DOCUMENTS

| | | | |
|---|---|---|---|
| JP | 2003-521985 | | 7/2003 |
| JP | 2004-070179 | | 3/2004 |
| JP | 2004-510467 | | 4/2004 |
| JP | 2004-226277 | | 8/2004 |
| JP | 2004-296736 | | 10/2004 |
| JP | 2004-532526 | | 10/2004 |
| JP | 2004-327760 | | 11/2004 |
| JP | 2005-501589 | | 1/2005 |
| JP | 2005253478 | | 9/2005 |
| WO | WO 88/01150 | | 2/1988 |
| WO | WO 88/02020 | | 2/1988 |
| WO | WO 92/16142 | | 10/1992 |
| WO | WO 95/16387 | | 6/1995 |
| WO | WO/96/13208 | * | 5/1996 |
| WO | WO 9613208 | | 5/1996 |
| WO | WO 97/01985 | | 1/1997 |
| WO | WO 98/43071 | | 10/1998 |
| WO | WO 00/18290 | | 4/2000 |
| WO | WO 00/42911 A1 | | 7/2000 |
| WO | WO 00-59374 | | 10/2000 |
| WO | WO 01/13790 | | 3/2001 |
| WO | WO 01/30414 | | 5/2001 |
| WO | WO 01/58347 | | 8/2001 |
| WO | WO 02/17780 | | 3/2002 |
| WO | WO 02/26123 | * | 4/2002 |
| WO | WO 0226123 | | 4/2002 |
| WO | WO 02/089664 | | 11/2002 |
| WO | WO 03/020129 | | 3/2003 |
| WO | WO 03/068060 | | 8/2003 |
| WO | WO 03/077761 | | 9/2003 |
| WO | WO 2004/034898 | | 4/2004 |
| WO | WO 2005/011488 | | 2/2005 |
| WO | WO 2006/094168 | | 9/2006 |

OTHER PUBLICATIONS

European Extended Search Report of European Application No. 12163719.3, mailing date of Jun. 18, 2012, in 6 pages.
Burritt, Mary F.; Current Analytical Approaches to Measuring Blood Analytes; vol. 36; No. 8(B); 1990.
European Examination Report dated Apr. 1, 2010, re EP App. No. 08 744 412.1-2319.
European Examination Report dated Mar. 18, 2011, re EP App. No. 08 744 412.1-2319.
European Examination Report dated Sep. 2, 2010, re EP App. No. 08 744 412.1-2319.
European Extended Search Report re EPO App. No. 10162402.1, SR dated Aug. 9, 2010.
Hall, et al., Jeffrey W.; Near-Infrared Spectrophotometry: A New Dimension in Clinical Chemistry; vol. 38; No. 9; 1992.
Japanese First Office Action (Notice of Reasons for Rejection), re JP App. No. 2007-558207, dated Jun. 28, 2011.
Japanese First Office Action (Notice of Reasons for Rejection), re JP App. No. 2007-558247, dated Jun. 28, 2011.
Japanese Office Action (Notice of Allowance), re JP App. No. 2007-558247, dated Oct. 24, 2011.
Japanese Office Action (Notice of Reasons for Rejection) re JP App. No. 2007-558246, dated Jun. 28, 2011.
Japanese Office Action (Notice of Reasons for Rejection), re JP App. No. 2007-558238, dated Jun. 28, 2011.
Japanese Office Action re JP Application No. 2007-558249, dated Jul. 19, 2011.
Japanese Office Action re JP Application No. 2007-558249, dated Nov. 8, 2011.
Japanese Office Action re JP Application No. Jp 2007-558208, dated Aug. 23, 2011.
Japanese Office Action re JP Application No. Jp 2007-558248, dated Nov. 8, 2011.
Japanese Office Action re JP Application No. 2007-558209, dated Oct. 25, 2011.
Japanese Office Action re JP Application No. 2007-558245, dated Oct. 25, 2011.
Japanese Office Action, re JP Application No. 2007-558237, dated Aug. 2, 2011.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse OXimetry in the Measurement of Hemoglobin Fractions; vol. 2676, date unknown.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
PCT International Search Report; PCT/US2006/007387; Date of Mailing Jul. 17, 2006; pp. 1-9.
PCT International Search Report; PCT/US2006/007388; Date of Mailing Jul. 17, 2006; pp. 1-9.
PCT International Search Report; PCT/US2006/007389; Date of Mailing Jul. 17, 2006; pp. 1-9.
PCT International Search Report; PCT/US2006/007506; Date of Mailing Jul. 17, 2006; pp. 1-10.
PCT International Search Report; PCT/US2006/007516, mailed on Jan. 11, 2007, in 4 pages.
PCT International Search Report; PCT/US2006/007536; Date of Mailing Jul. 17, 2006; pp. 1-9.
PCT International Search Report; PCT/US2006/007537; Date of Mailing Jul. 17, 2006; pp. 1-10.
PCT International Search Report; PCT/US2006/007538; Date of Mailing Jul. 17, 2006; pp. 1-9.
PCT International Search Report; PCT/US2006/007539; Date of Mailing Jul. 17, 2006; pp. 1-9.
PCT International Search Report; PCT/US2006/007540; Date of Mailing Jul. 17, 2006; pp. 1-9.
PCT International Search Report; PCT/US2006/007958; Date of Mailing Jul. 17, 2006; pp. 1-8.
PCT Search Report of International Application No. PCT/US2008/058327, Mailing Date of Jun. 30, 2009, in 12 pages.
Schmitt, Joseph M.; Simple Photon Diffusion Anaylsis of the Effects of Multiple Scattering on Pulse Oximetry; Mar. 14, 1991; revised Aug. 30, 1991.
Schmitt, Joseph M.; Zhou, Guan-Xiong; Miller, Justin, Measurement of Blood Hematocrit by Dual-wavelength Near-IR Photoplethysmography, published May 1992, Proc. SPIE vol. 1641, p. 150-161, Physiological Monitoring and Early Detection Diagnostic Methods, Thomas S. Mang; Ed. (SPIE homepage), in 12 pages.
Schnapp, et al., L.M.; Pulse Oximetry. Uses and Abuses.; Chest 1990; 98; 1244-1250001 10.1378/Chest.98.5.1244.
Notice of Reasons for Rejection for Japanese Application No. 2007-558237 dated Oct. 16, 2012, in 5 pages.
Notice of Reasons for Rejection for Japanese Application No. 2007-558245 dated Oct. 29, 2013, in 5 pages.
Office Action in European Application No. 12163719.3 dated Feb. 6, 2013, in 4 pages.

* cited by examiner

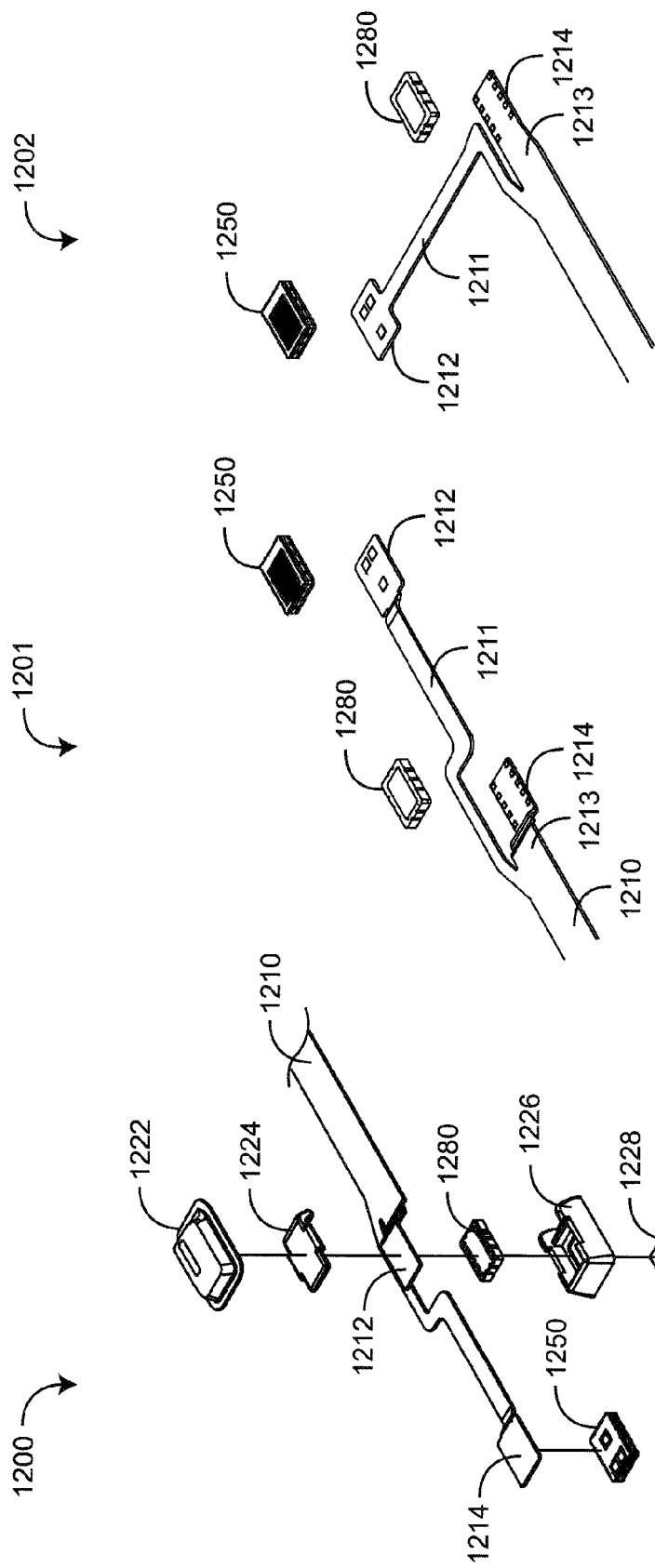

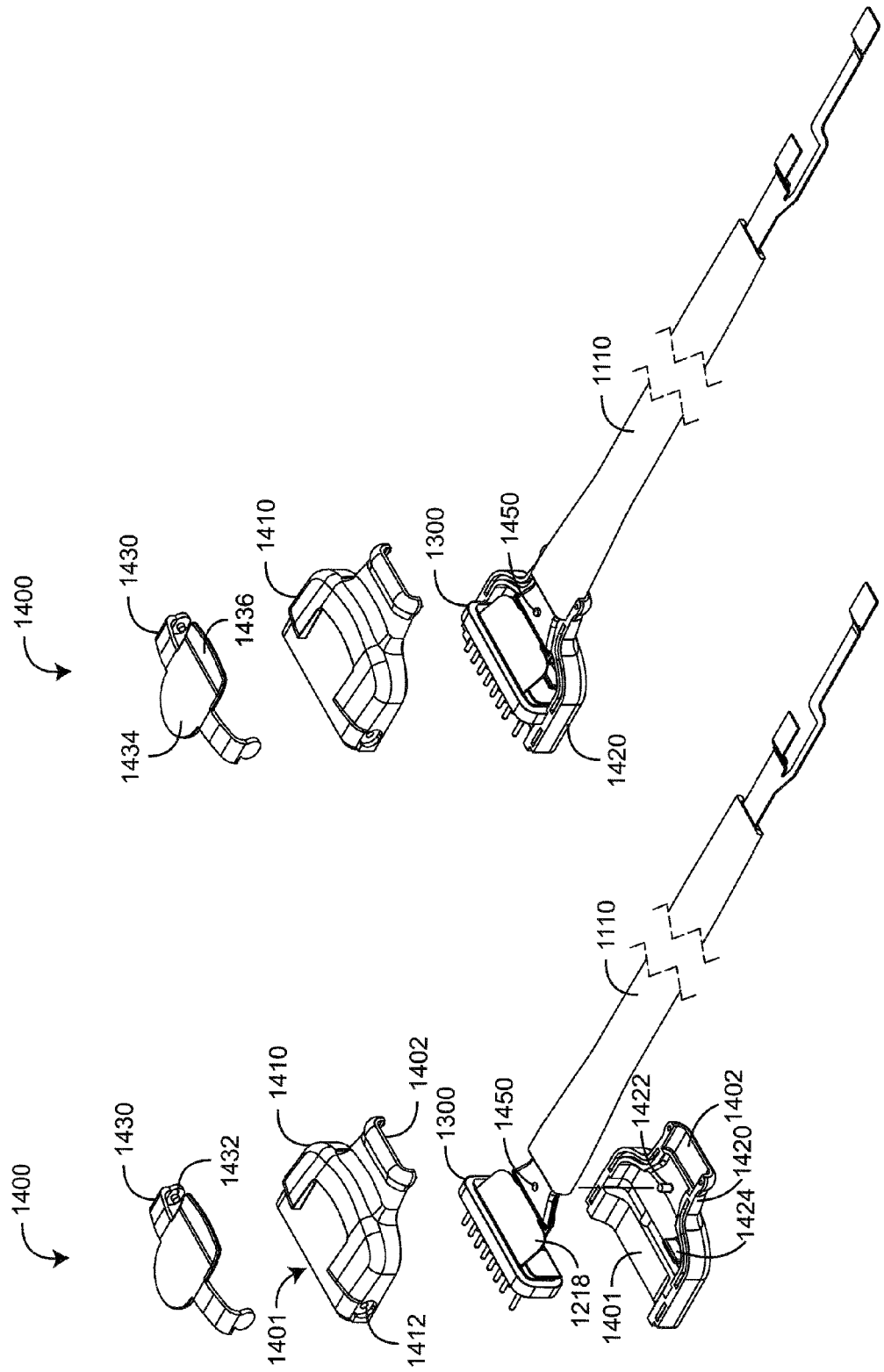

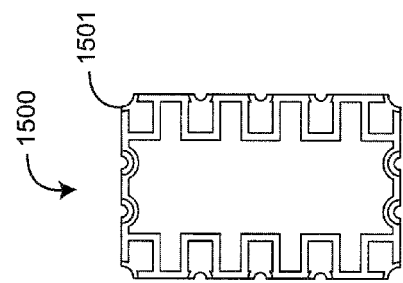
FIG. 16D
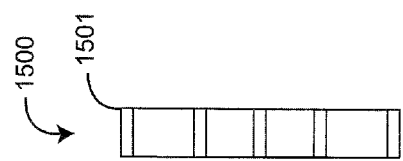
FIG. 16C
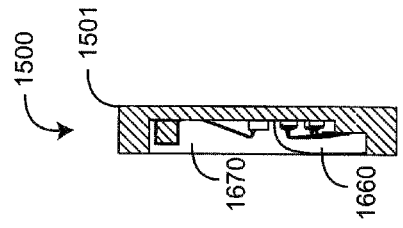
SECTION A-A
FIG. 16B
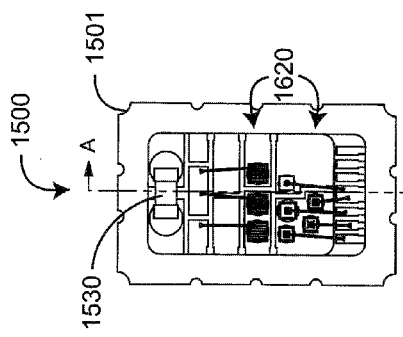
FIG. 16A
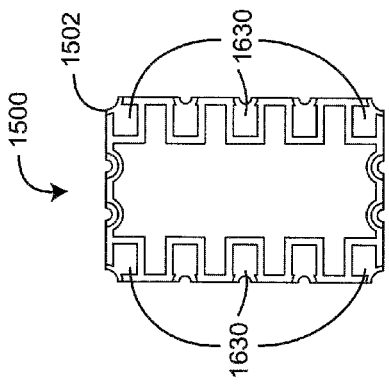
FIG. 16H
FIG. 16G
SECTION B-B
FIG. 16F
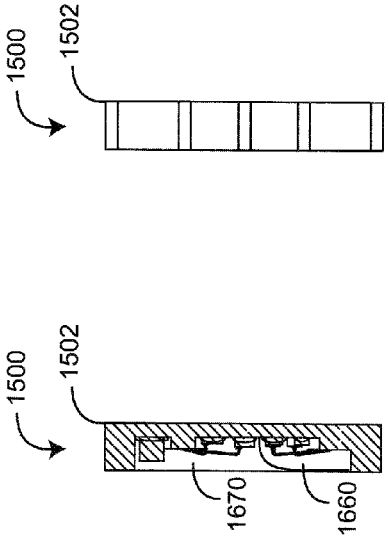
FIG. 16E

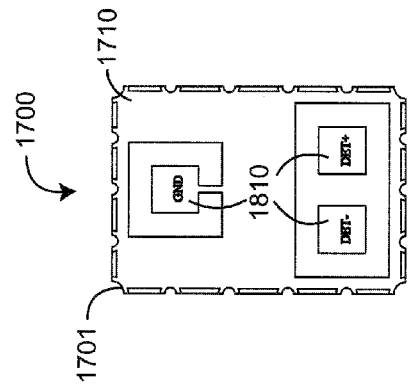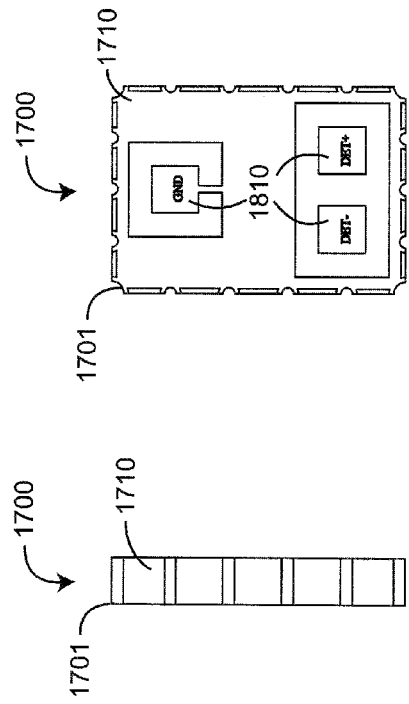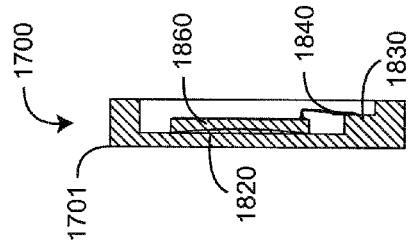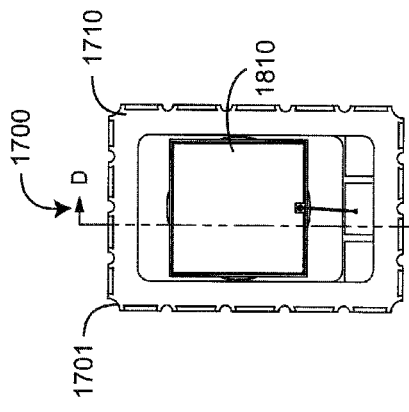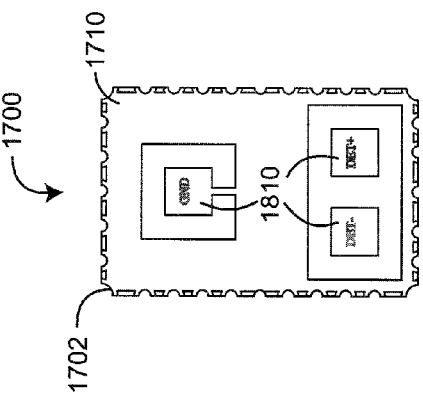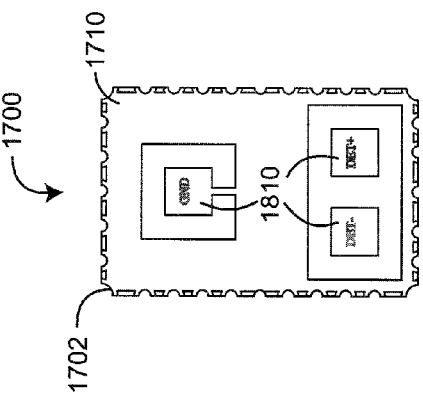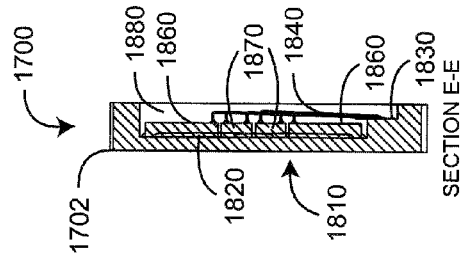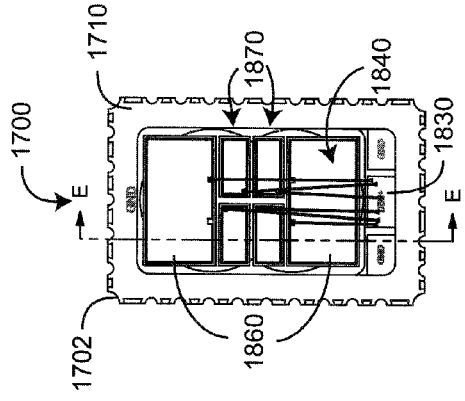

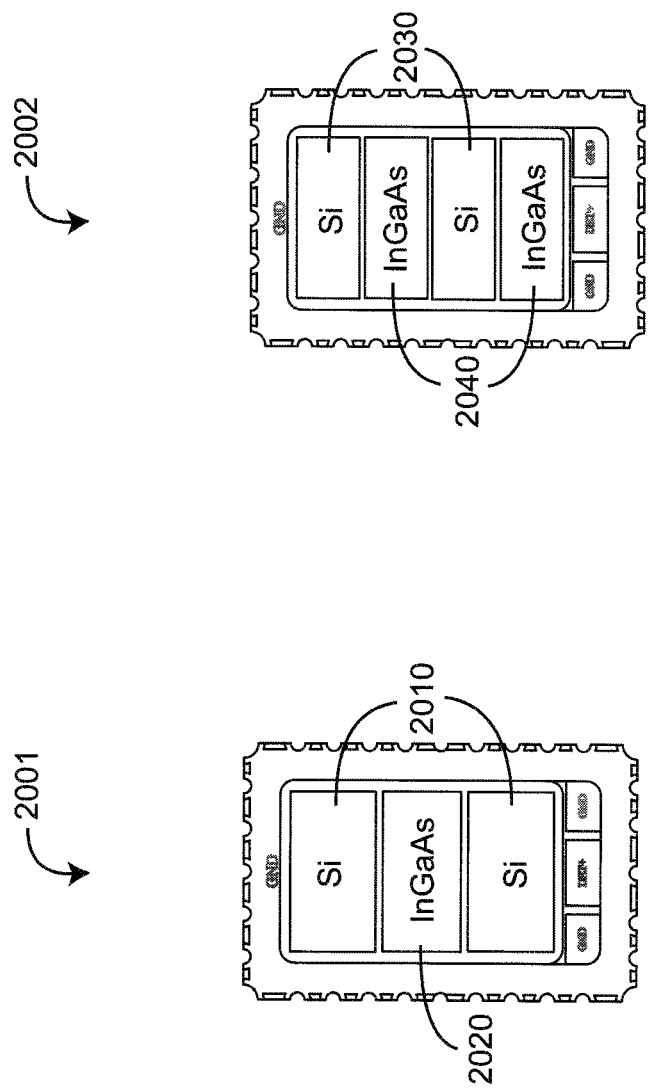

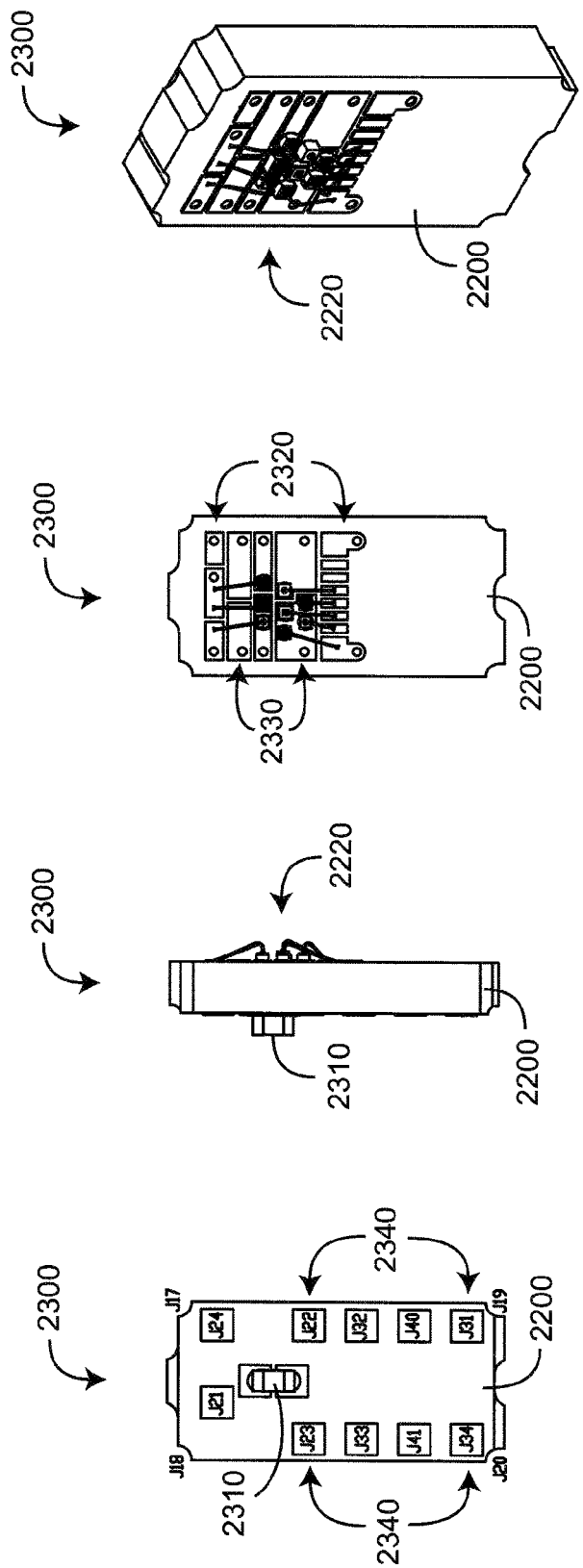

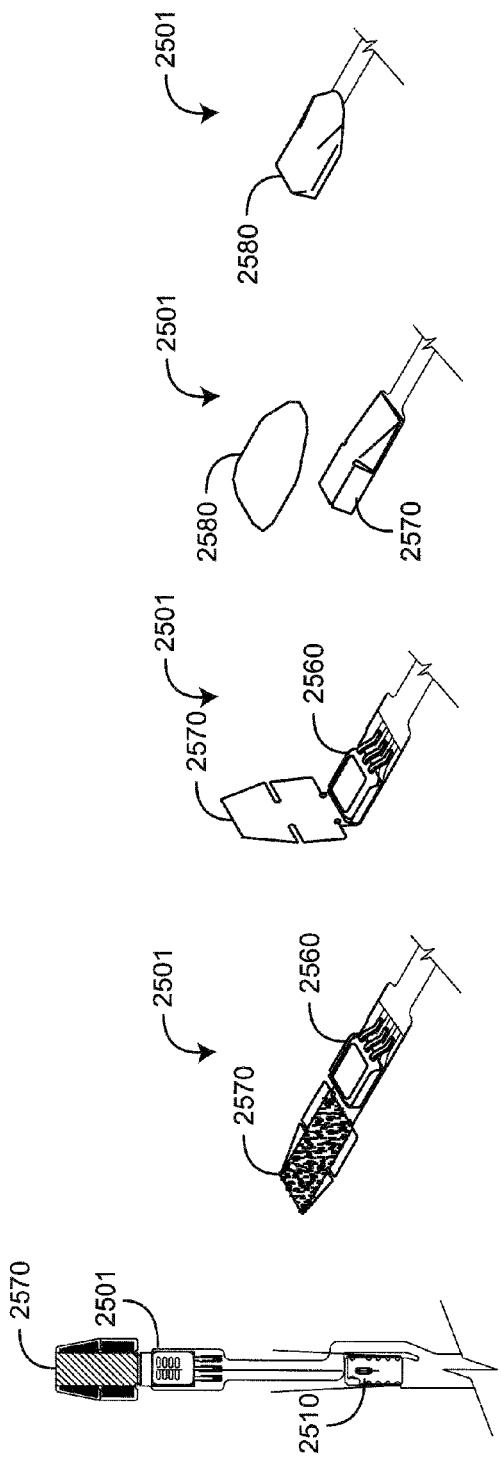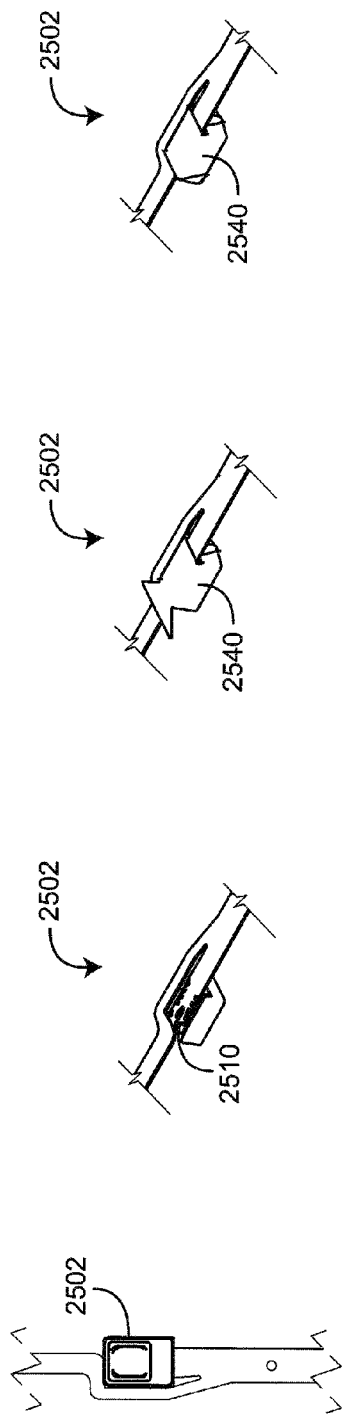
FIG. 26A FIG. 26B FIG. 26C FIG. 26D FIG. 26E
FIG. 26F FIG. 26G FIG. 26H FIG. 26I

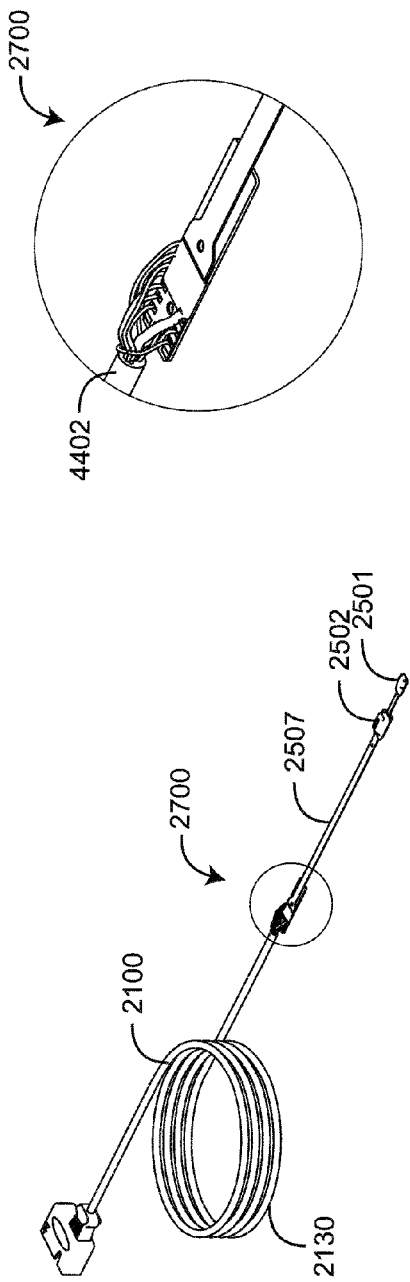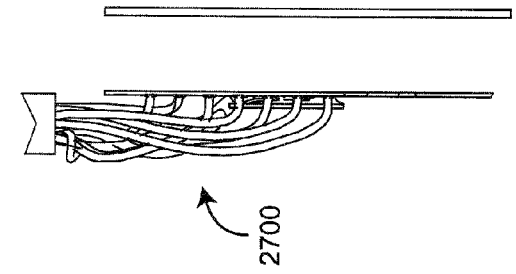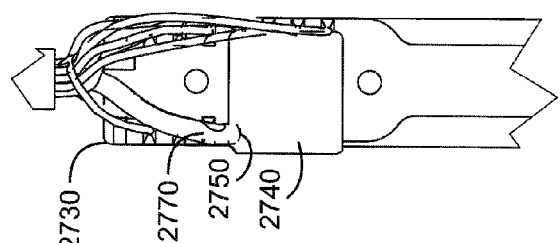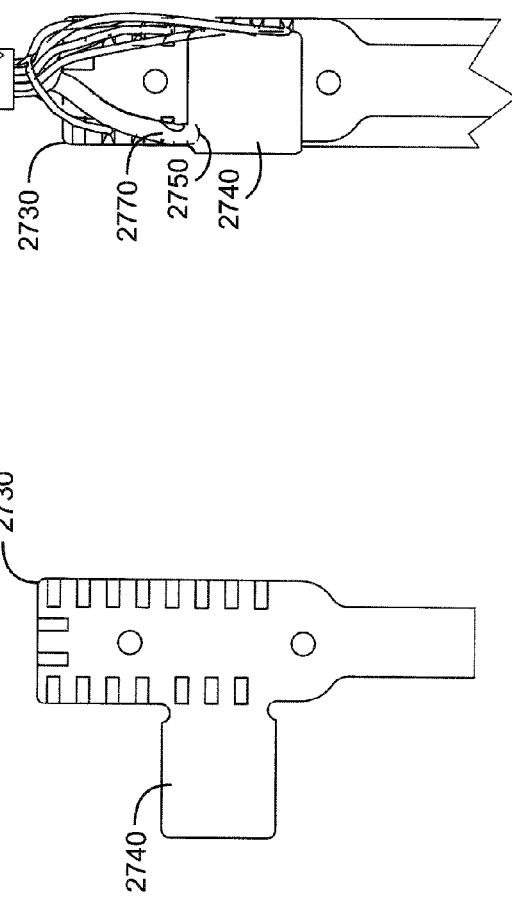

MULTIPLE WAVELENGTH OPTICAL SENSOR

PRIORITY CLAIM TO RELATED PROVISIONAL APPLICATIONS

The present application claims priority benefit under 35 U.S.C. §119(e) to U.S. Provisional patent application Ser. No. 60/920,474, filed Mar. 27, 2007, titled Disposable Multiple Wavelength Optical Sensor, No. 60/923,630, filed Apr. 14, 2007, titled Disposable Multiple Wavelength Optical Sensor, and No. 61/033,007, filed Mar. 2, 2008, titled Multiple Wavelength Optical Sensor. All of the above-referenced applications are hereby incorporated by reference herein.

INCORPORATION BY REFERENCE OF COPENDING RELATED CASES

The present disclosure is generally related to U.S. Provisional Application Ser. No. 60/998,659, filed Oct. 12, 2007, titled Ceramic Emitter Substrate; U.S. Provisional Application Ser. No. 60/979,658, filed Oct. 12, 2007, titled Ceramic Detectors; U.S. Provisional Application Ser. No. 60/979,674, filed Oct. 12, 2007, titled Connector Assembly; U.S. Design patent application Ser. No. 29/296,064, filed Oct. 12, 2007, titled Connector Assembly; U.S. Design patent application Ser. No. 29/296,067, filed Oct. 12, 2007, titled Connector Assembly; U.S. Provisional patent application Ser. No. 61/032,936, filed Feb. 29, 2008, titled Connector Assembly; and U.S. Design patent application Ser. No. 29/304,439, filed Feb. 29, 2008, titled Connector. All of the above-referenced applications are hereby incorporated by reference herein.

BACKGROUND OF THE INVENTION

Pulse oximetry systems for measuring constituents of circulating blood have gained rapid acceptance in a wide variety of medical applications including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are attached to a patient tissue site, such as a finger. The patient cable transmits drive signals to these emitters from the monitor, and the emitters respond to the drive signals to transmit light into the tissue site. The detector generates a signal responsive to the emitted light after attenuation by pulsatile blood flow within the tissue site. The patient cable transmits the detector signal to the monitor, which processes the signal to provide a numerical readout of physiological parameters such as oxygen saturation ($SpO_2$) and pulse rate. Advanced physiological monitoring systems utilize multiple wavelength sensors and multiple parameter monitors to provide enhanced measurement capabilities including, for example, the measurement of carboxyhemoglobin (HbCO), methemoglobin (HbMet) and total hemoglobin (Hbt).

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and titled Multiple Wavelength Sensor Emitters and U.S. patent application Ser. No. 11/366,208, filed Mar. 1, 2006 and titled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo.

SUMMARY OF THE INVENTION

There is a need to noninvasively measure multiple physiological parameters, other than, or in addition to, oxygen saturation and pulse rate. For example, hemoglobin parameters that are also significant are total hemoglobin (Hbt) and the percentage of carboxyhemoglobin and methemoglobin. Other blood parameters that may be amenable to noninvasive optical sensor measurement are fractional oxygen saturation, bilirubin and blood glucose, to name a few.

One aspect of a physiological sensor is an emitter that emits light having a plurality of wavelengths. A detector generates an output signal responsive to the emitted light after absorption by tissue. An attachment assembly removably attaches the emitter and the detector to tissue. A spacer provides a predetermined gap between the emitter and tissue when the emitter is attached to tissue. A light scattering medium is disposed in a optical path between the emitter and tissue. The spacer and the light scattering medium provide at least a substantially uniform illumination of tissue by the emitted light for each of the wavelengths. In various embodiments, the light scattering medium comprises glass beads mixed with an encapsulant disposed proximate the spacer. The light scattering medium comprises microspheres mixed with an epoxy disposed proximate the emitter. The emitter comprises an array of at least eight light emitting diodes emitting light generally centered around eight unique wavelengths. The emitter comprises an array of at least thirteen light emitting diodes emitting light generally centered around at least twelve unique wavelengths. The detector comprises at least one Si photodiode and at least one InGaAs photodiode connected in parallel. The detector comprises two Si photodiodes and four InGaAs photodiodes all connected in parallel. The light emitting diodes emit light within a first range of about 620-905 nm and within a second range of about 1040-1270 nm.

Another aspect of a physiological sensor comprising an emitter configured to radiate light having a plurality of wavelengths into a tissue site. The emitter comprises a plurality of LEDs disposed within an emitter ceramic substrate. A detector is configured to receive the light after absorption by pulsatile blood flow within the tissue site. The detector generates a sensor signal capable of being processed by a patient monitor so as to derive total hemoglobin (Hbt). The detector comprises a plurality of photodiodes disposed within a detector ceramic substrate. A first set of the photodiodes is responsive to a first set of the wavelengths and a second set of the photodiodes is responsive to a second set of the wavelengths. In various embodiments a diffuser scatters the radiated light so that a tissue site is uniformly illuminated across all of the wavelengths. A first encapsulate containing glass beads is mounted in a spacer proximate the emitter ceramic substrate. A second encapsulate mixed with microspheres is disposed on the LEDs within the emitter ceramic substrate. The photodiodes comprise at least one Si photodiode and at least one InGaAs photodiode connected in parallel. The LEDs radiate light generally centered around at least twelve unique wavelengths. The LEDs are mounted in an array of at least thirteen LEDs connected within an electrical grid. The twelve unique wavelengths comprise eight wavelengths within a first range of about 620-905 nm. and four wavelengths within a second range of about 1040-1270 nm.

A further aspect of a physiological sensor comprises a light source that radiates light having a plurality of wavelengths, a diffuser that scatters the radiated light so that a tissue site is uniformly illuminated across all of the wavelengths, and at least one detector that generates a sensor signal responsive to the radiated light after tissue attenuation. In an embodiment, the light source comprises a ceramic substrate having conductors arranged as an electrical grid and a plurality of LEDs mounted within the ceramic substrate in an array. In other embodiments, the diffuser comprises a first encapsulant having microspheres disposed over the LEDs; and a second encapsulant having glass beads disposed proximate the ceramic substrate. A spacer is disposed proximate the ceramic substrate so as to form a gap between the LEDs and the tissue site. A connector connects to a patient cable so as to communicate the sensor signal to a monitor. A flexible coupling has an optical end proximate the light source and the detector and a connector end proximate the connector. The flexible coupling has conductors that communicate the sensor signal from the optical end to the connector end.

BRIEF DESCRIPTION OF THE DRAWINGS

FIGS. 12A-C are exploded perspective views of an optical assembly;

FIGS. 14A-D are exploded perspective views, and perspective and side views, respectively, of a connector assembly;

FIGS. 16A-H are top, cross-sectional, side and bottom views, respectively, of emitter embodiments;

FIGS. 18A-H are top, cross-sectional, side and bottom views, respectively, of detector components;

FIGS. 20A-B are top views of detector component embodiments;

FIGS. 23A-D are bottom, side, top and perspective views of an emitter assembly;

FIGS. 26A-I are assembly views for an optical assembly;

FIGS. 27A-E are views of a cable connection assembly; and

DETAILED DESCRIPTION OF THE PREFERRED EMBODIMENTS

Figure 1:
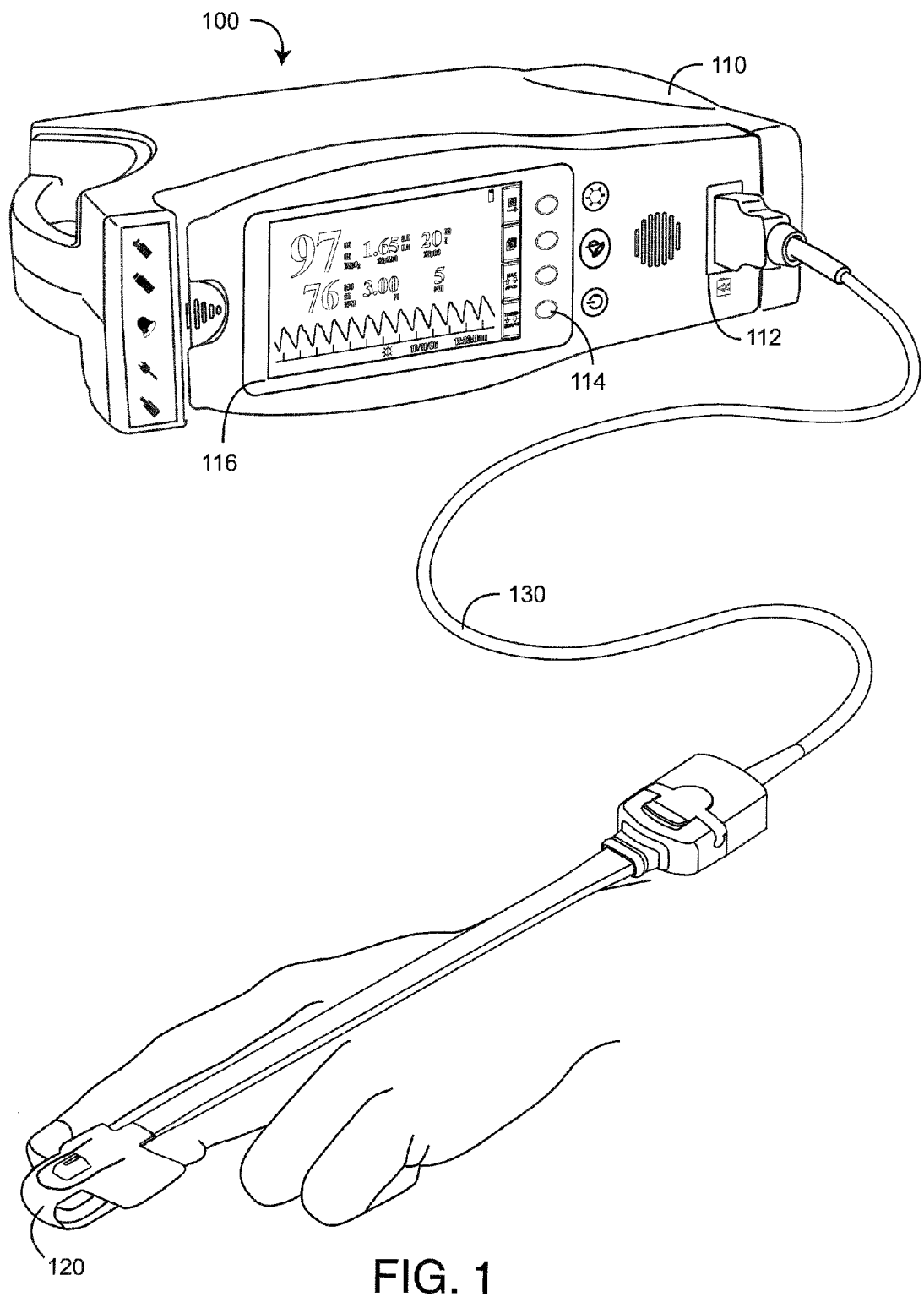
FIG. 1 is a perspective view of a physiological measurement system.

FIG. 1 illustrates a physiological measurement system 100 having a monitor 110 and a multiple wavelength optical sensor 120 with enhanced measurement capabilities as compared with conventional pulse oximetry. In particular, the multiple wavelength optical sensor 120 allows the measurement of various blood constituents and related parameters in addition to oxygen saturation and pulse rate. Alternatively, the multiple wavelength optical sensor 120 allows the measurement of oxygen saturation and pulse rate with increased accuracy or robustness as compared with conventional pulse oximetry.

In one embodiment, the optical sensor 120 is configured to plug into a monitor sensor port 112 via a patient cable 130. Monitor keys 114 provide control over operating modes and alarms, to name a few. A display 116 provides readouts of measured parameters, such as oxygen saturation, pulse rate, HbCO, HbMet and Hbt to name a few. Other blood parameters that may be measured to provide important clinical information are fractional oxygen saturation, bilirubin and blood glucose, to name a few.

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Figure 2:
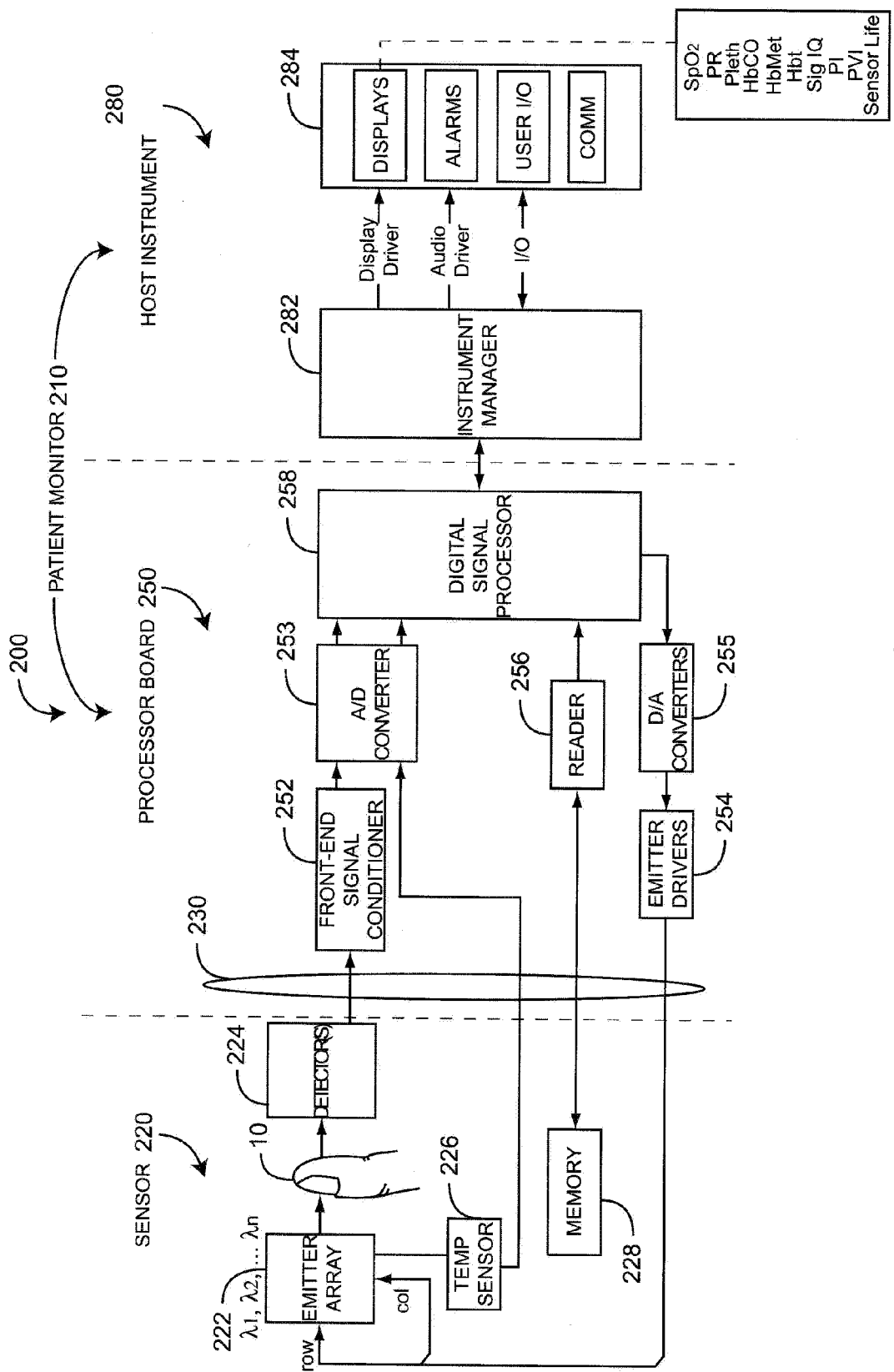
FIG. 2 is a general block diagram of a physiological measurement system.

FIG. 2 illustrates a block diagram a physiological measurement system 200. This measurement system includes a monitor 210 and an optical sensor 220 communicating via a patient cable 230. The monitor 210 has one or more processor boards 250 communicating with a host instrument 280. Generally, the processor board 250 communicates with the sensor 220 so as to control the emission of light into a tissue site 10. Also the processor board 250 receives and processes a corresponding sensor signal responsive to the emitted light after scattering and absorption by tissue site constituents. Accordingly, the processor board 250 derives physiological parameters relating to pulsatile blood flow within the tissue site and communicates values for those parameters to the host instrument 280. Generally, the host instrument 280 provides user I/O and communications with external devices so as to define operating conditions and communicate those conditions to the processor board 250. The host instrument 280 also transfers parameter values from the processor board for display and for triggering alarms.

In an embodiment, the optical sensor 220 includes an emitter array 222, at least one detector 224, a temperature sensor 226 and a memory 228. The emitter array 222 irradiates a tissue site 10 with multiple wavelength light. One or more detectors 224 detect the light after attenuation by the tissue site 10. The temperature sensor 226 is located so as to detect the bulk temperature of the emitters within the emitter array, so as to accurately determine emitter wavelengths, as described below. The memory 228 can include any of a wide variety of memory devices known to an artisan from the disclosure herein, including an EPROM, an EEPROM, a flash memory, a ROM, a non-volatile RAM and a two-terminal serial memory device, to name a few, and combinations of the same. The memory 228 can advantageously store a wide variety of sensor-related information, including sensor type, manufacturer information, sensor characteristics including wavelengths emitted, wavelength correction data, emitter drive requirements, demodulation data, calculation mode data, calibration data and sensor life data to name a few. The memory can also store software such as scripts and executable code, encryption information, monitor and algorithm upgrade instructions and enabled parameters.

Although described herein with respect to various disposable sensor embodiments, a sensor may be reusable, resposable (partially reusable/partially disposable), adhesive or non-adhesive, or a transmittance, reflectance or transflectance sensor. Further, a sensor may be configured for a variety of tissue sites such as a finger, hand, foot, forehead or ear or for attachment to multiple tissue sites, including multiple-head sensors capable of simultaneous multi-site measurements.

As shown in FIG. 2, the processor board 250 includes a front end signal conditioner 252, an analog-to-digital (A/D) converter 253, a digital signal processor (DSP) 258, a memory reader 256, emitter drivers 254 and digital-to-analog (D/A) converters 255. In general, the drivers 254 convert digital control signals into analog drive signals capable of activating the emitter array 222. The front-end 252 and A/D converter 253 transform composite analog intensity signal(s) from light sensitive detector(s) 224 into digital data input to the DSP 258. In an embodiment, the DSP 258 is adapted to communicate via a reader 256 with one or more information elements such as the memory 228.

According to an embodiment, the DSP 258 comprises a processing device based on the Super Harvard ARChitecture ("SHARC"), such as those commercially available from Analog Devices. However, the DSP 258 can comprise a wide variety of data and/or signal processors capable of executing programs for determining physiological parameters from input data. According to an embodiment, the processor board 250 may comprise one or more microcontrollers (not shown) for board management, including, for example, communications of calculated parameter data and the like to the host instrument 280.

Also shown in FIG. 2, the host instrument 280 communicates with the processor board 250 to receive signals indicative of the physiological parameter information calculated by the DSP 258. The host instrument 280 preferably includes one or more display devices, alarms, user I/O and communication ports 284. The alarms may be audible or visual indicators or both. The user I/O may be, as examples, keypads, touch screens, pointing devices or voice recognition devices. The displays may be indicators, numerics or graphics for displaying one or more of a pulse rate, plethysmograph data, signal quality, perfusion index and blood constituents values, such as $SpO_2$, carboxyhemoglobin (HbCO), methemoglobin (HbMet) and total hemoglobin (Hbt), or the like. The host instrument 280 may also be capable of storing or displaying historical or trending data related to one or more of the measured values or combinations of the measured values. A patient monitor is disclosed in U.S. App. No. 11/367,033, filed on Mar. 1, 2006, titled Noninvasive Multi-Parameter Patient Monitor, which is assigned to Masimo and incorporated by reference herein.

Figure 3:
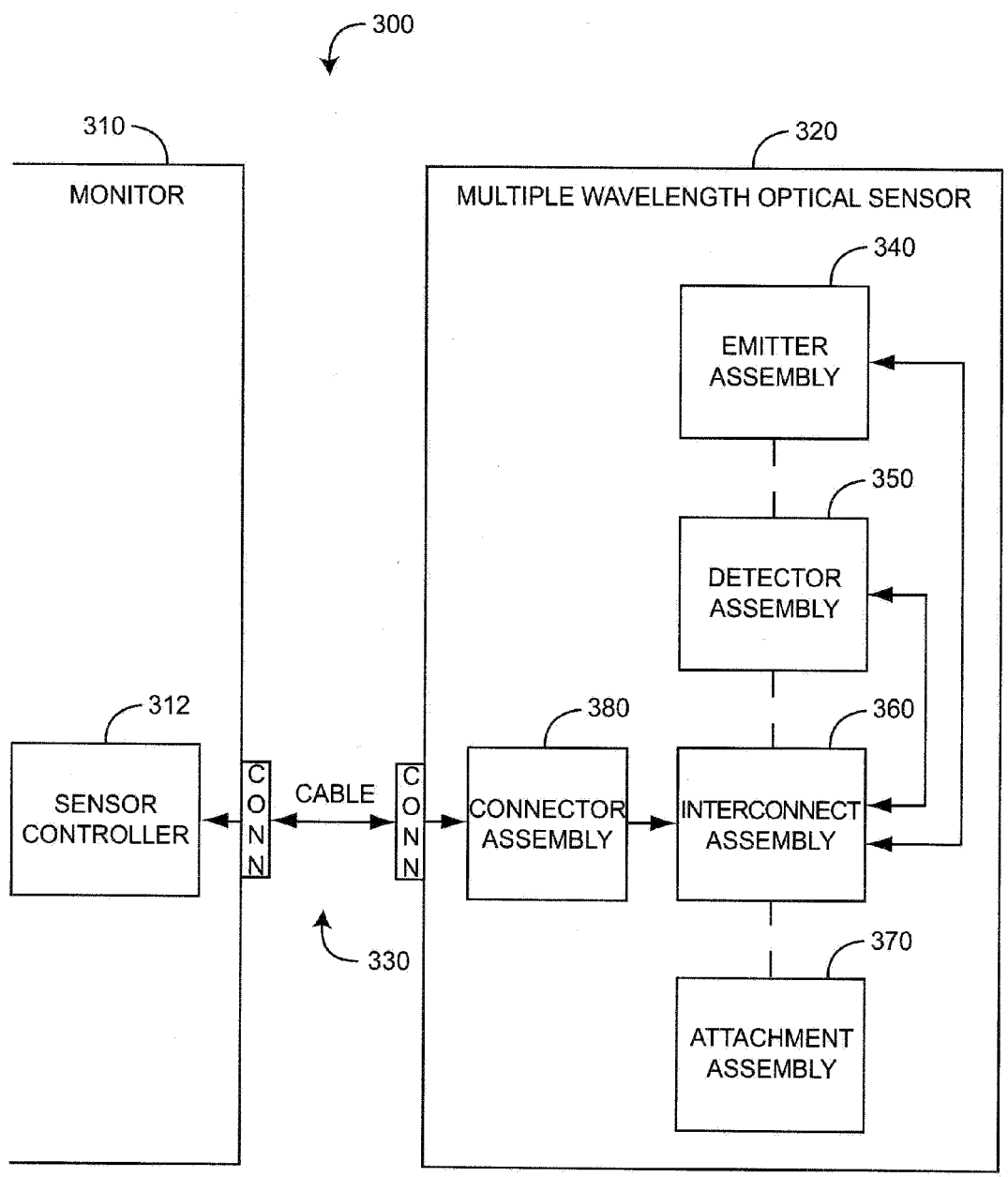
FIG. 3 are block diagrams of a multiple wavelength optical sensor and a monitor.

FIG. 3 illustrates a physiological measurement system 300 having a monitor 310 and a multiple wavelength sensor 320. The sensor 320 has an emitter assembly 340, a detector assembly 350, an interconnect assembly 360, an attachment assembly 370 and a connector assembly 380. The monitor 310 has a sensor controller 312 that communicates with the sensor 320 via a cable 330. As but one example, the sensor controller 312 may include emitter drivers, detector signal conditioning circuitry, A/D and D/A connectors, and a DSP incorporated onto a processor board, such as described with respect to FIG. 2, above.

As shown in FIG. 3, the emitter assembly 340 responds to drive signals received from the sensor controller 312 so as to emit light having a plurality of wavelengths. The detector assembly 350 provides a sensor signal to the sensor controller 312 in response to the emitted light after absorption by a tissue site. The interconnect assembly 360 mechanically mounts the emitter assembly 340 and the detector assembly 350 and provides electrical communication between the cable 330 and these assemblies 340, 350. The attachment assembly 370 attaches the emitter assembly 340 and detector assembly 350 to a tissue site. The connector assembly 380 provides a mechanical and electrical interface to the connector at one end of the cable 330. A tape assembly example of an attachment assembly is described with respect to FIGS. 11A-B, below. A contact assembly example of a connector assembly is described with respect to FIGS. 13-14, below.

Figure 4:
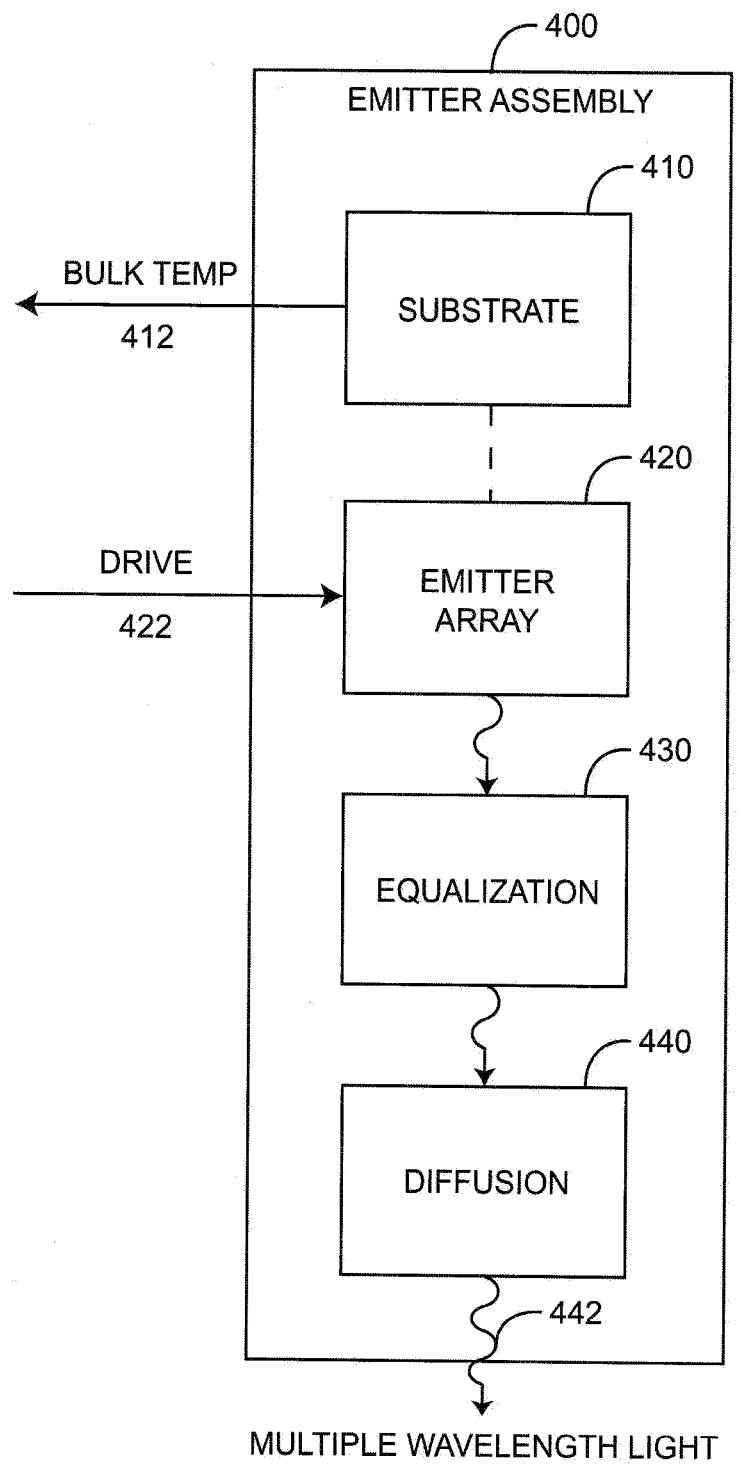
FIG. 4 is a general block diagram of an emitter assembly.

FIG. 4 illustrates an emitter assembly 400 having a substrate 410, an emitter array 420, an equalization 430 and a diffusion 440. The emitter array 420 has multiple light emitting sources, each activated by drive signals 422. The light emitting sources are capable of generating light 442 having multiple wavelengths. The equalization 430 accounts for differences in emitter intensity and tissue absorption of the light across the multiple wavelengths so as to at least partially equalize wavelength-dependent variations in intensity at the detector. The substrate 410 provides a physical mount for the emitter array and emitter-related equalization and an electrical connection between the emitter array and an interconnect assembly, such as described above. Advantageously, the substrate 410 also maintains a uniform bulk temperature measurement so as to calculate the operating wavelengths for the light emitting sources. One example of an emitter array embodiment 420 is described with respect to FIG. 6, below. One example of equalization 430 is described with respect to encapsulants, below. Examples of substrates 410 are described with respect to ceramic and board substrates, below.

Figure 5:
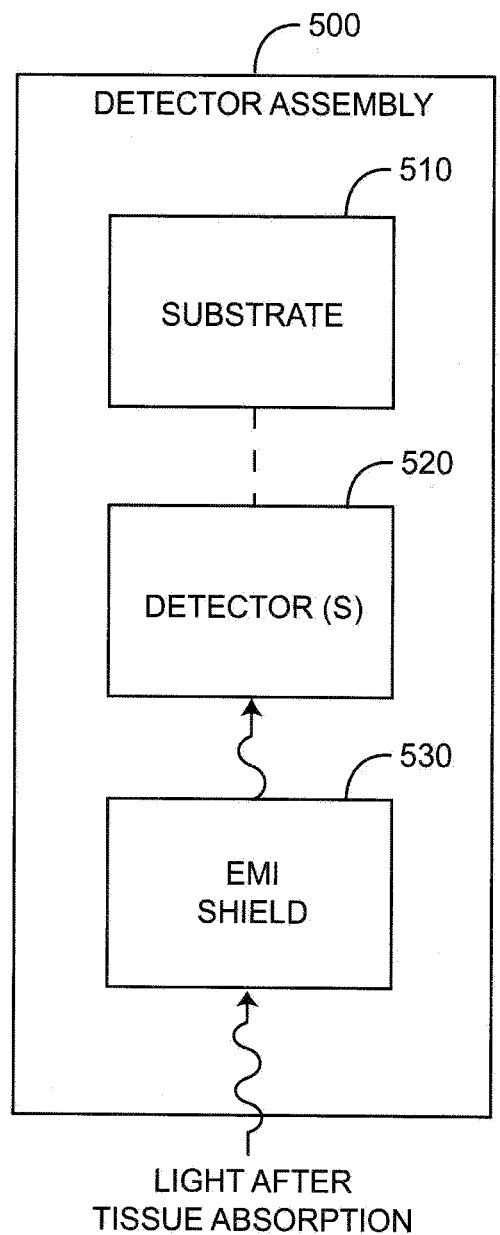
FIG. 5 is a general block diagram of a detector assembly.

FIG. 5 illustrates a detector assembly 500 including a substrate 510, detector(s) 520 and an EMI shield 530. The substrate 510 acts as a mechanical support for, and provides electrical contacts to, the detector(s) 520. In an embodiment, the substrate 510 acts as an electrical insulator allowing the detector(s) 520 to be electrically isolated from EMI shielding 530 applied to a detector component. In an embodiment, the substrate 510 is a ceramic material.

Figure 6:
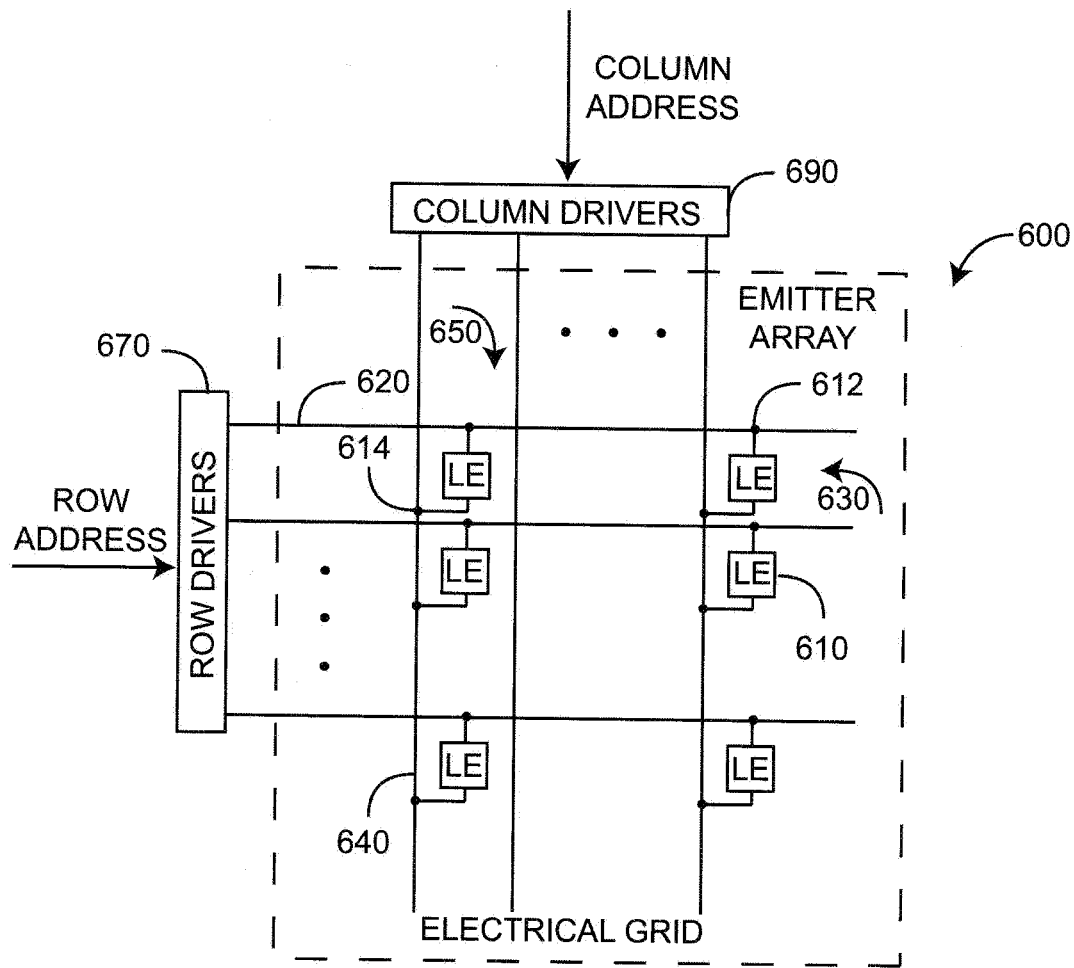
FIG. 6 is a general block diagram of an emitter array.

FIG. 6 illustrates an emitter array 600 having multiple light emitters (LE) 610 capable of emitting light having multiple wavelengths. Row drivers 670 and column drivers 690 are electrically connected to the light emitters 610 and activate one or more light emitters 610 by addressing at least one row 620 and at least one column 640 of an electrical grid. In one embodiment, the light emitters 610 each include a first contact 612 and a second contact 614. The first contact 612 of a first subset 630 of light emitters is in communication with a first conductor 620 of the electrical grid. The second contact 614 of a second subset 650 of light emitters is in communication with a second conductor 640.

Figure 7:
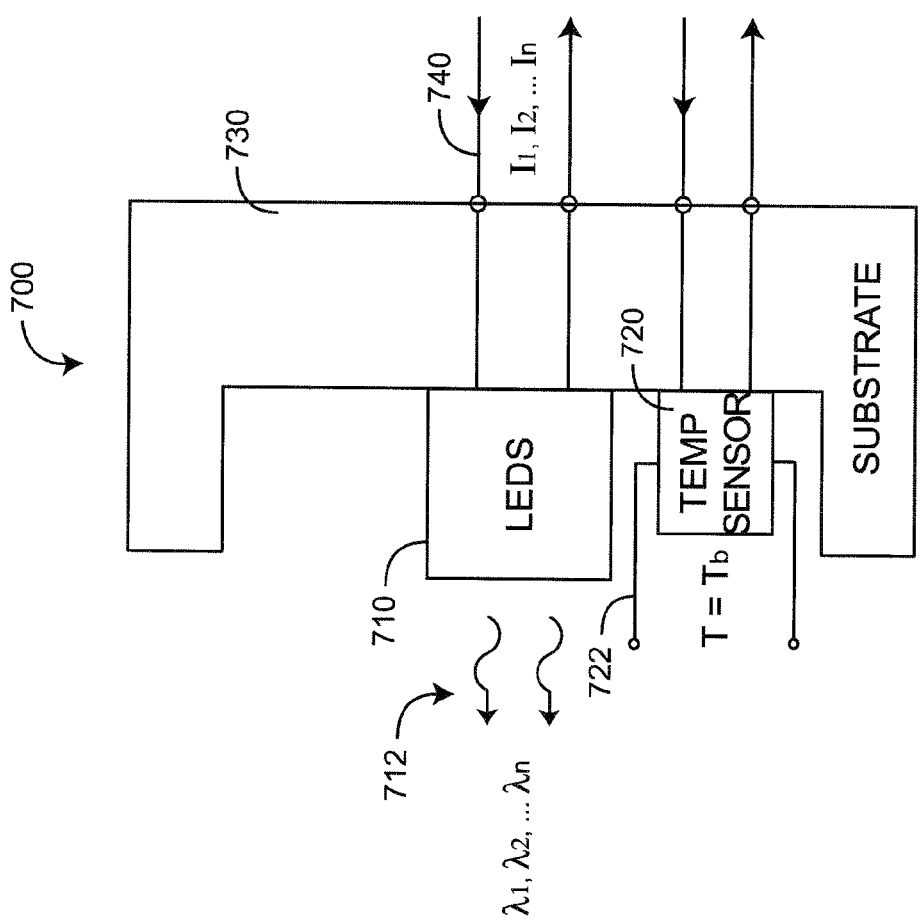
FIG. 7 is a block diagram of an emitter component.

FIG. 7 illustrates an example of an emitter assembly 700 having light emitting diodes 710, a temperature sensor 720 and a substrate 730. The substrate 730 provides a thermal mass so as to stabilize a bulk temperature for the LEDs 710. A temperature sensor 720 is thermally coupled to the substrate 730 so as to output, say, a current responsive to the bulk temperature $T_b$. The LED wavelengths 712 are determinable as a function of the drive currents 740 and the temperature sensor output 722. In an embodiment, the substrate 730 is a ceramic material or, alternatively, a circuit board material having multiple materialization layers for thermal mass.

In one embodiment, an operating wavelength $\lambda_a$ of each LED 710 is determined according to EQ. 1:

$$\lambda_a = f(T_b, I_{drive}, \Sigma I_{drive}) \tag{1}$$

where $T_b$ is the bulk temperature, $I_{drive}$ is the drive current for a particular LED, as determined by a sensor controller, and $\Sigma I_{drive}$ is the total drive current for all LEDs. In another embodiment, temperature sensors are configured to measure the temperature of each LED 710 and an operating wavelength $\lambda_a$ of each light emitter is determined according to EQ. 2:

$$\lambda_a = f(T_a, I_{drive}, \Sigma I_{drive}) \tag{2}$$

where $T_a$ is the temperature of a particular light emitter, $I_{drive}$ is the drive current for that light emitter and $\Sigma I_{drive}$ is the total drive current for all light emitters.

In yet another embodiment, an operating wavelength for each LED is determined by measuring the junction voltage for each LED 710. In a further embodiment, the temperature of each LED 710 is controlled, such as by one or more Peltier cells coupled to each LED 710, and an operating wavelength for each LED 710 is determined as a function of the resulting controlled temperature or temperatures. In other embodiments, the operating wavelength for each LED 710 is determined directly, for example by attaching a charge coupled device (CCD) to each light emitter or by attaching a fiberoptic to each light emitter and coupling the fiberoptics to a wavelength measuring device, to name a few.

Figure 8:
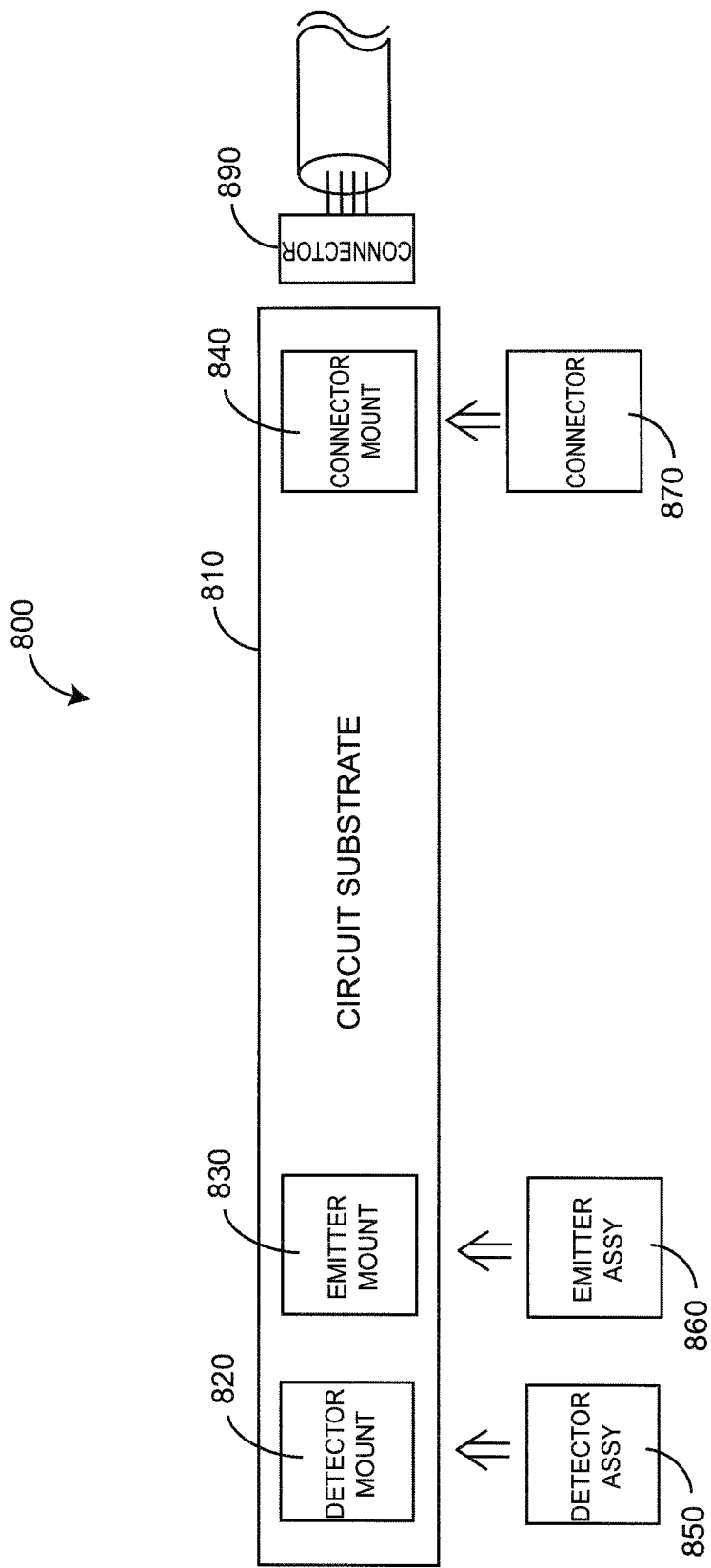
FIG. 8 is a block diagram of a circuit substrate.

FIG. 8 illustrates an interconnect assembly 800 having a circuit substrate 810, an emitter mount 830, a detector mount 820 and a connector mount 840. The emitter mount 830 mounts and electrically connects to an emitter assembly 860 having multiple light emitters. The detector mount 820 mounts and electrically connects to a detector assembly 850 having a detector. The connector mount 840 attaches a connector 870 having conductors that mate with a patient cable connector 890. A first plurality of conductors disposed on the circuit substrate 810 electrically interconnect the emitter mount 830 and the connector 870. A second plurality of conductors disposed on the circuit substrate 810 electrically interconnect the detector mount 820 and the connector 870.

Figure 9:
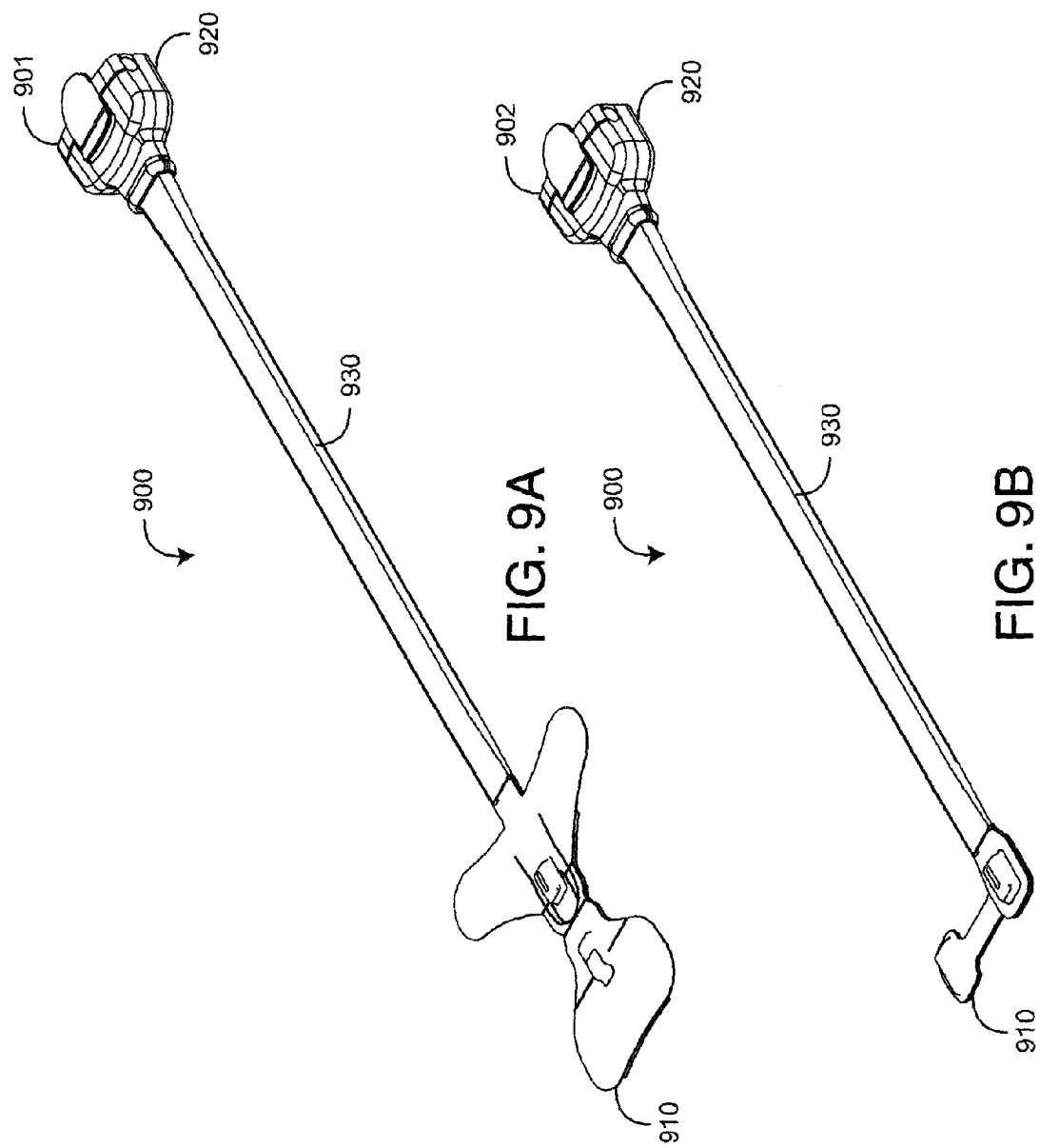
FIGS. 9A-B are perspective views of multiple wavelength optical sensor embodiments.

FIGS. 9A-B illustrate embodiments of a multiple wavelength optical sensor. In particular, illustrated are a disposable sensor 900 including an adult/pediatric sensor 901 configured for finger placement and an infant/neonate sensor 902 configured for toe, foot or hand placement. Each sensor 900 has a tape end 910 and an opposite connector end 920 electrically and mechanically interconnected via a flexible coupling 930. The tape end 910 attaches an emitter and detector to a tissue site, as described below. The emitter illuminates the tissue site and the detector generates a sensor signal responsive to the light after tissue absorption, such as absorption by pulsatile arterial blood flow within the tissue site. The sensor signal is communicated via the flexible coupling 930 to the connector end 920. The connector mates with a cable (not shown) that communicates the sensor signal to a monitor (not shown). The monitor calculates a variety of physiological parameters from the detector signal, such as pulse rate (PR), oxygen saturation ($SpO_2$), carboxyhemoglobin (HbCO), methemoglobin (HbMet) and total hemoglobin (Hbt), to name a few. A sensor configured for measurement of at least some of the above-mentioned physiological parameters is described in U.S. Provisional Application Ser. No. 60/920,474, filed Mar. 27, 2007, titled Disposable Multiple Wavelength Optical Sensor; and U.S. Provisional Application Ser. No. 60/923,630, filed Apr. 14, 2007, titled Disposable Multiple Wavelength Optical Sensor, both applications incorporated by reference herein.

Figure 10:
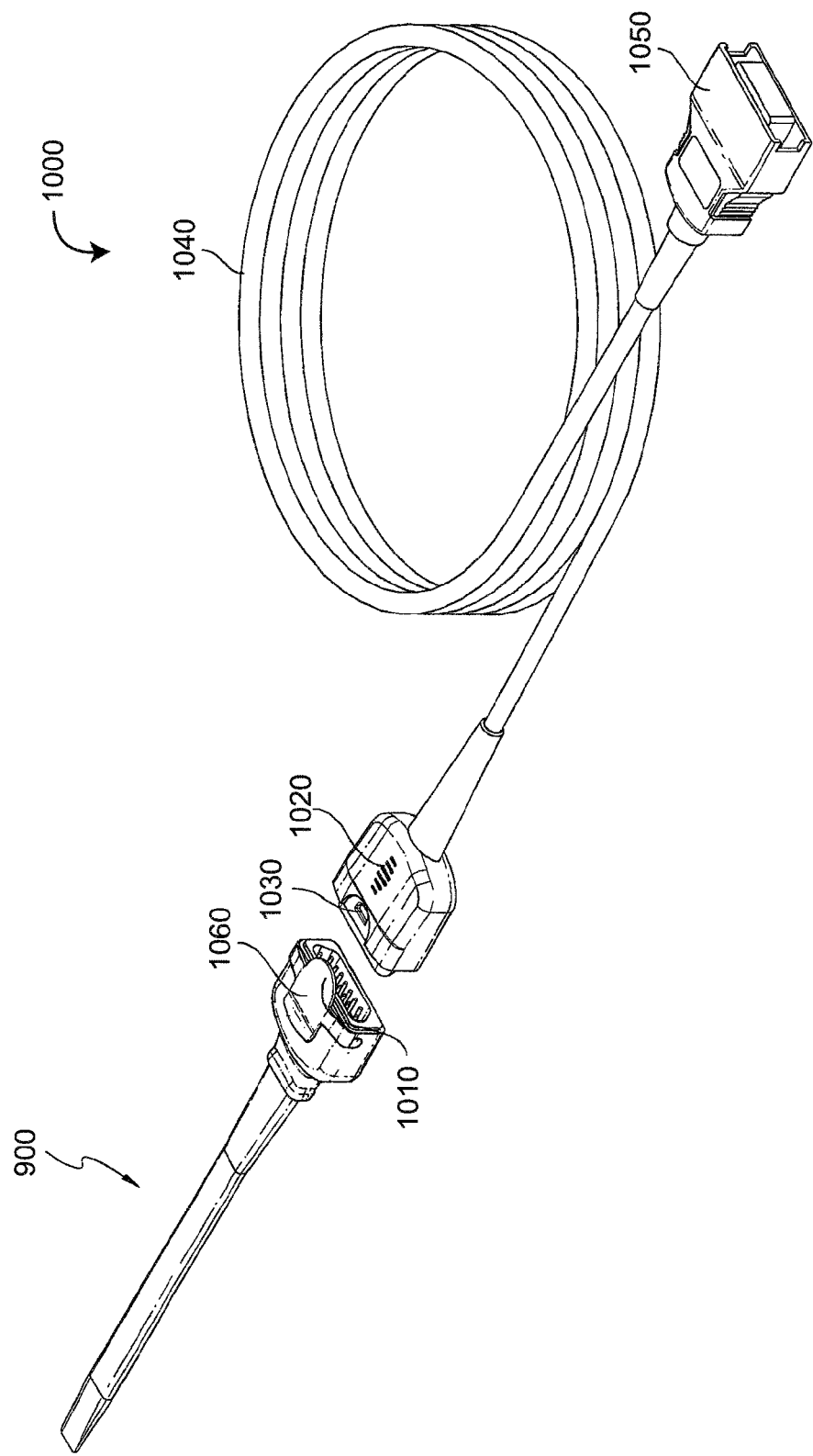
FIG. 10 is a perspective view of a patient cable and corresponding sensor connector.

FIG. 10 illustrates an optical sensor 900 connecting with a patient cable 1000. In the illustrated embodiment, the sensor 900 connects to the patient cable 1000 via a 15-pin sensor connector 1010 that mates with a 15-socket patient cable connector 1020. In various embodiments, the sensor connector 1010 may have all of the pins electrically active, and, in other embodiments, only a subset of the pins may be active and used to communicate sensor signals. For example, in one embodiment only 9 pins are active. In other embodiments, the sensor connector may be a standard $SpO_2$ sensor, having, for example, a 9-pin mini-D connector, which is well known in the art. A latch 1060 disposed on the sensor connector 1010 is configured to engage a catch 1030 disposed on the patient cable connector 1020 so as to releasably hold the sensor connector 1010 and patient cable connector 1020 together. The sensor connector 1010 and patient cable connector 1020 are connected by pressing them together until the latch 1060 clicks into the catch 1030 and separated by pulling them apart while pressing downward on the latch 1060, thereby disengaging the latch 1060 from the catch 1030. In one embodiment, the monitor connector 1050 is a 20-pin DB connector. An example of a sensor connector is described with respect to FIGS. 13-14.

Figure 11A:
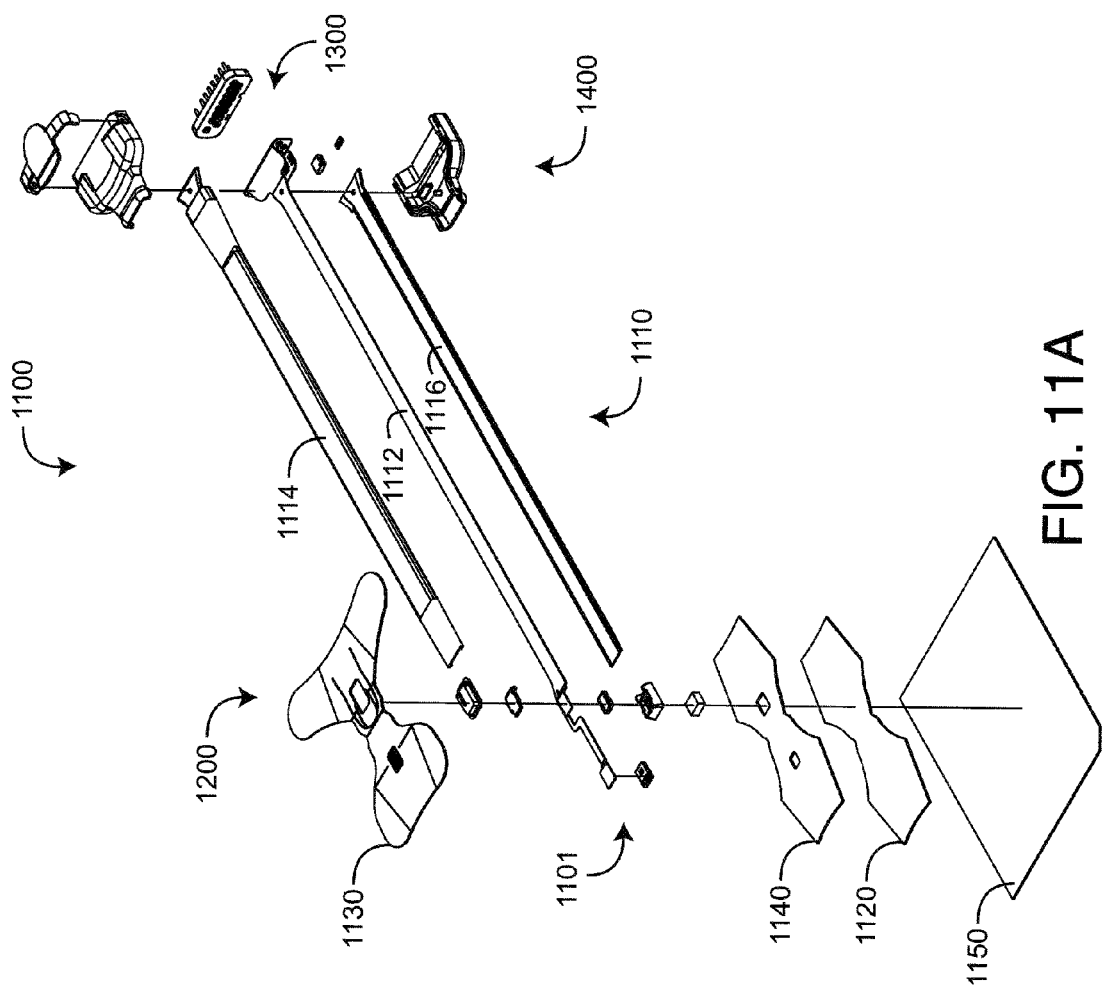
FIGS. 11A-B are exploded perspective views of multiple wavelength optical sensor embodiments.
Figure 11B:
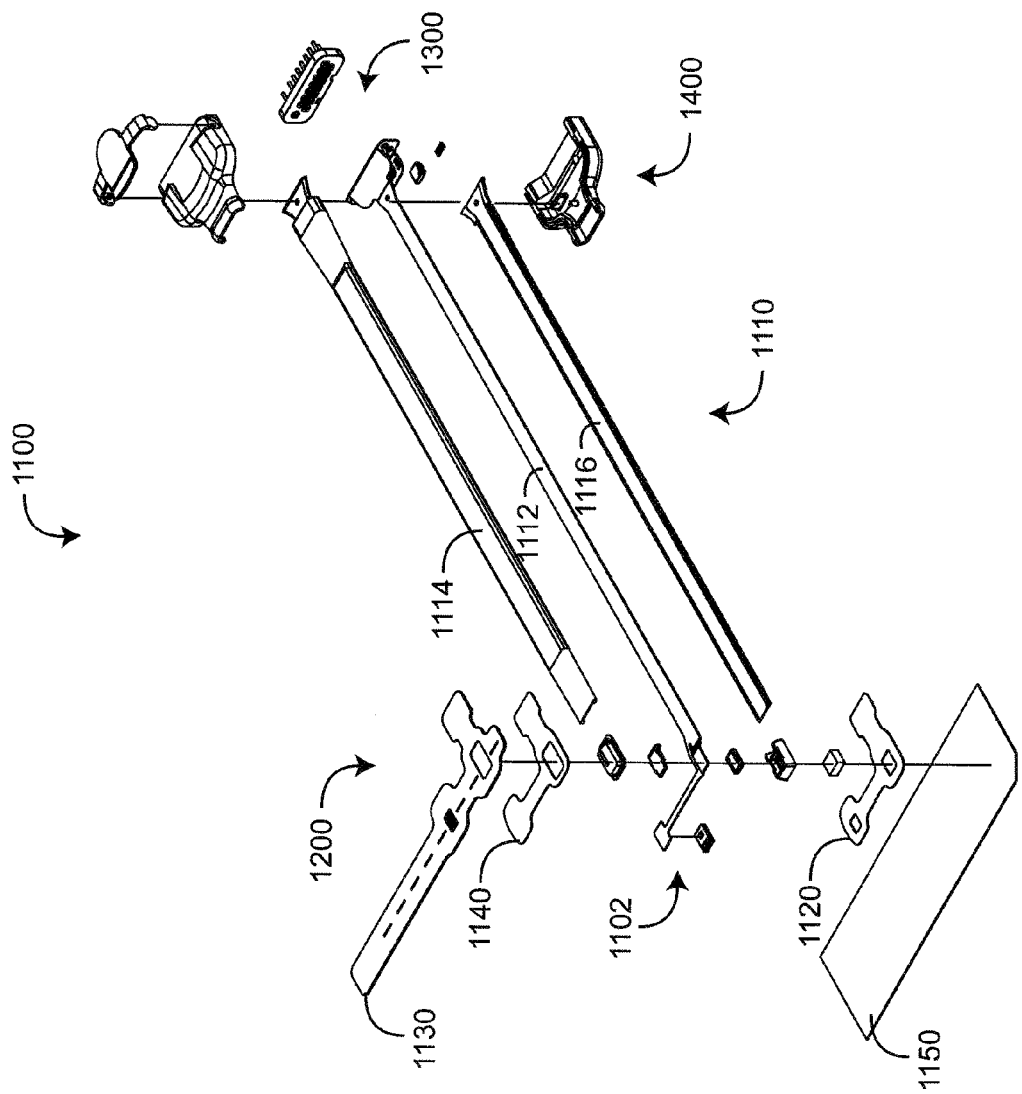

FIGS. 11A-B illustrate sensor assemblies 1100, including an "I" configuration 1101 for adult/pediatric sensors and an "L" configuration 1102 for infant/neonate sensors. A sensor assembly 1100 has a flexible coupling 1110 interconnecting optical components 1200 at an optical end and connector components 1300 at a connector end. The coupling 1110 includes a flex circuit 1112, a top sleeve 1114 and a bottom sleeve 1116. The top sleeve 1114 and bottom sleeve 1116 interlock to create a channel which encloses a flex circuit 1112. In one embodiment, the sleeve 1114, 1116 is comprised of silicone rubber. The flex circuit 1112 mounts the optical components 1200 and a contact assembly 1300 and provides electrical communications between the optical components 1200 and the connector components 1400, including the contact assembly 1300. In an embodiment, base-tape, center-tape, face-tape and release liner layers 1150 are attached to "two-up" untaped assemblies and then cut to shape so as to provide an attachment assembly at tape end 910 (FIGS. 9A-B) for tissue attachment, described above.

FIGS. 12A-C further illustrate optical components 1200 having emitter components 1220 and a detector 1250 mounted to a flex circuit 1210. The emitter components 1220 include a cover 1222, a light block 1224, an emitter 1280, a spacer 1226 and an encapsulant 1228. Advantageously, the spacer 1226 and encapsulant 1228 provide a relatively uniform illumination of a tissue site across all emitted wavelengths. In particular, the spacer 1226 provides a gap between the emitter 1280 and a tissue site, allowing emitted light from, say, individual LEDs of the emitter 1280 to spread as the multiple wavelength light propagates to a tissue site. Further, the encapsulant 1228 can be configured to diffuse or scatter emitted light as the light propagates to a tissue site. In an embodiment, the spacer 1226 gap is 70 mm. In an embodiment, the encapsulant 1228 contains 0.1 mm glass beads, 25% by weight, in a clear silicon RTV. In an embodiment, the emitter has an epoxy fill over LEDs incorporated within the emitter that contain microspheres so as to diffuse or scatter LED transmitted light, as described below. In an embodiment, an attenuation epoxy is dispersed over selected emitter LEDs so as to equalize intensities of the various LEDs, also as described, below. LED intensity equalization is disclosed in U.S. patent application Ser. No. 11/366,995, filed Mar. 1, 2006, titled Multiple Wavelength Sensor Equalization, incorporated by reference herein. In an embodiment, the encapsulant or LED fill or both provide notch filter characteristics according to emitted wavelengths so as to substantially attenuate secondary emissions from one or more LEDs.

As shown in FIGS. 12B-C, the flex circuit 1210 terminates a first solder plate 1212 which is generally rectangular and connected to and is slightly wider than a first connection arm 1211. In an "I" configuration 1201, the first connection arm 1211 bends along its length in order to accommodate a second solder plate 1214. In an "L" configuration 1202, the first connection arm 1211 has a generally right-angle bend away from the second solder plate 1214. The second solder plate 1214 terminates a second connection arm 1213. In an embodiment, the first solder plate 1212 has three solder pads arranged in a triangular fashion for connecting to corresponding detector solder pads. The second solder plate 1214 has ten smaller solder pads arranged in rows for connecting to corresponding emitter solder pads. It is well known in the art to include conductors and conductor paths on one or more sides of the flex circuit 1210. In various embodiments, the shape of the flex circuit 1210 may vary. For instance, in some embodiments, the flex circuit 1210 may vary in length and the bends, if any, may vary in characteristics.

Figure 13:
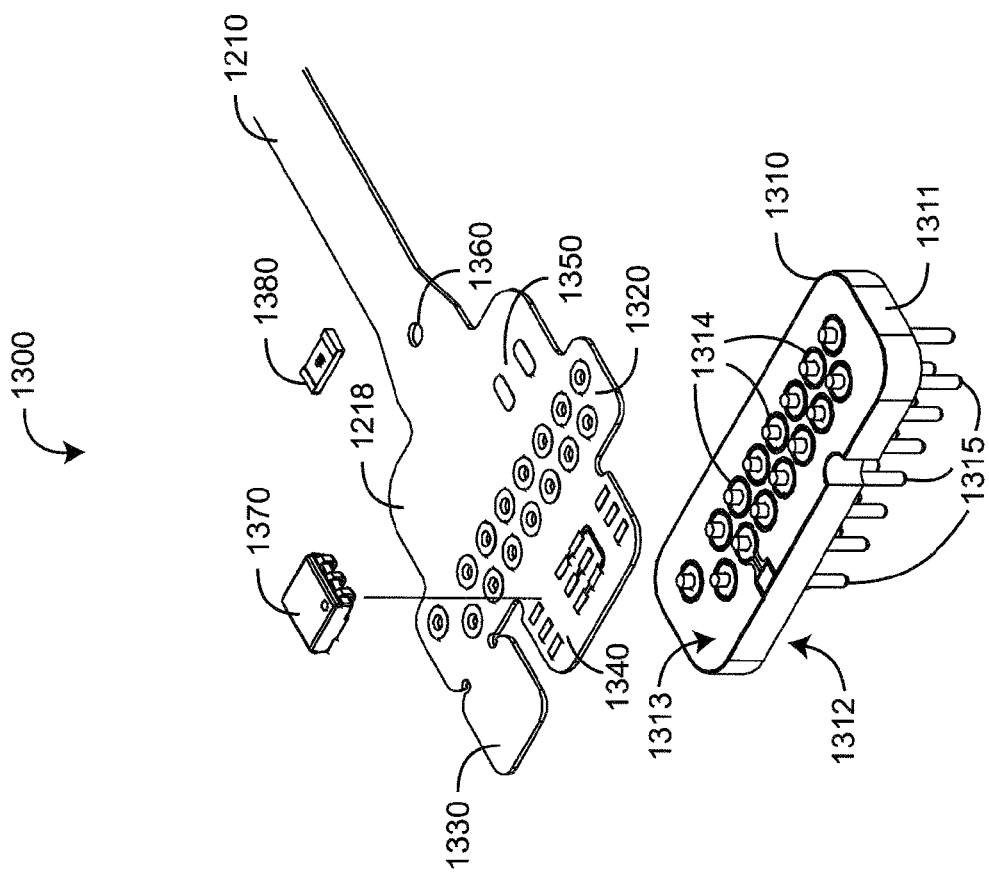
FIG. 13 is an exploded perspective view of a contact assembly.
Figure 14C:
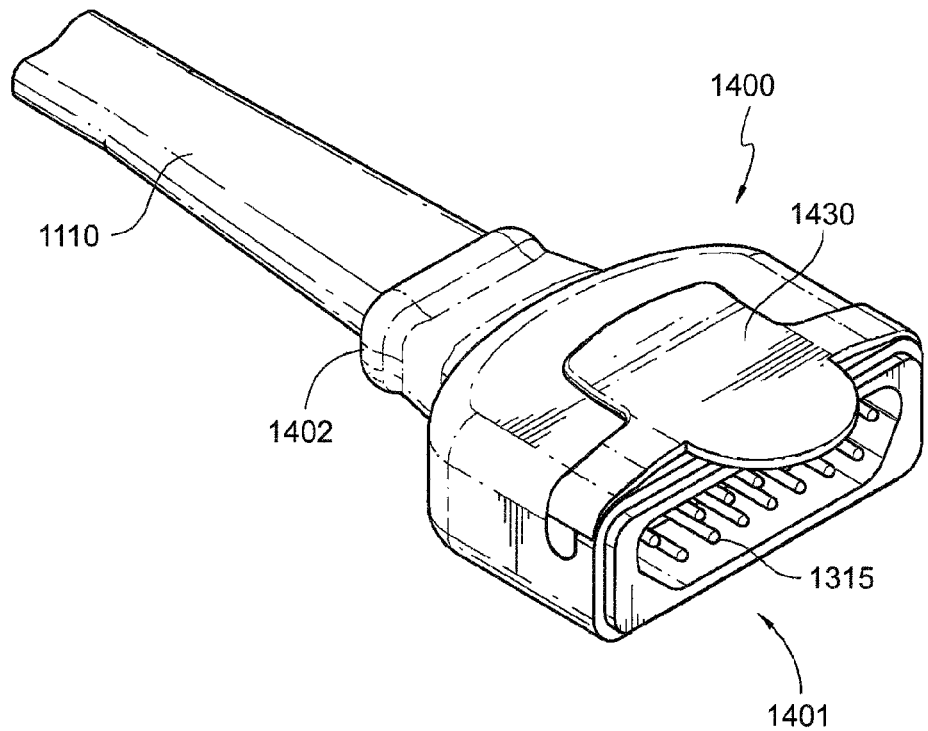
Figure 14D:
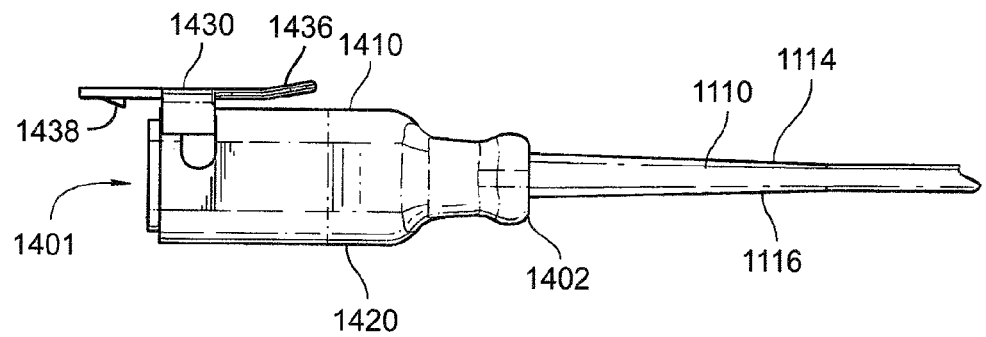

FIG. 13 illustrates a contact assembly 1300 having a connector plug 1310 that mates with a flex circuit connector plate 1218. The connector plate 1218 forms one end of the flex circuit 1210 in communication with solder plates 1212, 1214 (FIGS. 12B-C) at an opposite end of the flex circuit 1210. The connector plug 1310 has a generally rectangular base 1311 and pins 1315. The base 1311 has a front 1312, a back 1313 and pin apertures 1314 extending through the base 1311. The pin apertures 1314 are arranged in two rows, and the pins 1315 extend through the apertures 1314 so that a relatively long plug portion of the pins 1315 extends from base front 1312 and a relatively short solder portion of the pins 1315 extends from the base back 1313. The solder portion of the pins 1315 extend through and are fixedly soldered within corresponding connector plate apertures 1320. In one embodiment, the base 1311 is comprised of a PC-ABS blend and the pins 1315 are comprised of a brass, bronze or copper base with gold plating.

As shown in FIG. 13, the connector plate 1218 has plug apertures 1320, a flap 1330, memory pads 1340, resistor pads 1350 and a peg aperture 1360. The flap 430 folds over a detector pin portion of the plug apertures 1320 so as to provide shielding for detector pins, which communicate a sensor signal from the detector 1250 (FIGS. 12A-C) to a patient monitor. The peg aperture 1360 is configured to accommodate a shell peg 1422 (FIG. 14A), securing the flex circuit 1210 to the sleeve 1114, 1116 (FIGS. 11A-B) and connector shell 1410, 1420 (FIGS. 14A-B). At least one memory 1370 is soldered to the memory pads 1340. In one embodiment, the memory 1370 is a 20K EEPROM advantageously providing various sensor identification, diagnostic and control functions. In an embodiment, two 20K EEPROMs are utilized.

FIGS. 14A-D illustrate a connector 1400 having a top shell 1410, a bottom shell 1420, a clip 1430 and a contact assembly 1300. The connector front has a passageway 1401 that accommodates a mating patient cable connector. A positioning tab 1424 abuts the flex circuit connector plate 1218 (FIG. 13). Apertures 1412 secure the clip 1430 by accommodating clip pegs 1432. The connector back has a passageway 1402 that accommodates the flexible coupling 1110. A shell peg 1422 engages a sleeve aperture 1450, which secures the flex circuit 1112 and sleeve 1110 to the connector shell 1410, 1420. In one embodiment, the connector shell 1410, 1420 is a PC-ABS blend.

The clip 1430 has a sloping latch 1438 located underneath the clip front 1434 and a lever 1030 (FIG. 10) extending from the clip back. The latch 1438 snaps into a corresponding catch of a mating patient cable connector. Advantageously, the lever 1436 is rigidly connected to the clip front 1434 and corresponding latch 1438 so that pressing downward with a finger or thumb on the lever 1436 raises the latch so as to disengage it from the corresponding catch 1030 (FIG. 10). As such, the clip 1430 advantageously releasably holds the connector 1400 to a mating patient cable connector 1020 (FIG. 10) so as to reduce accidental disconnects and provide for relatively straightforward and efficient connection and release. In certain embodiments, the clip 1430 releases without depressing the lever 1436 when a threshold of tension is placed on the connection. This avoids equipment damage and injuries if a sensor is accidentally jerked by a patient. In one embodiment, the clip 1430 is comprised of a PC-ABS blend.

Figure 15A:
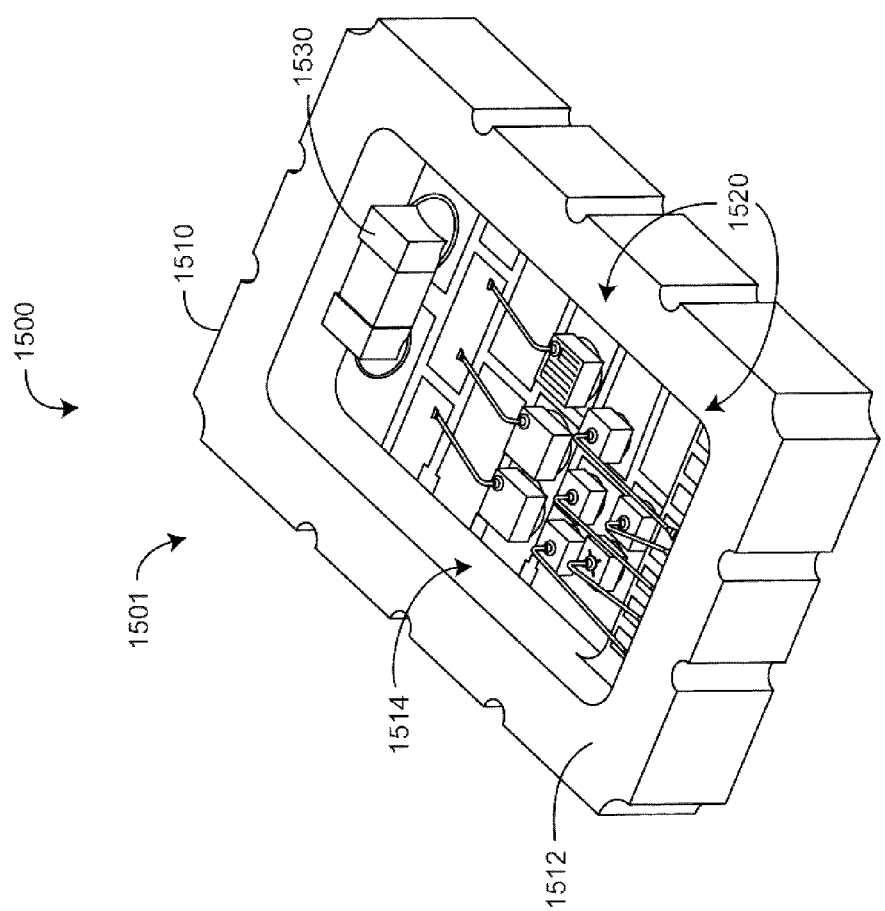
FIGS. 15A-B are perspective views of emitters.
Figure 15B:
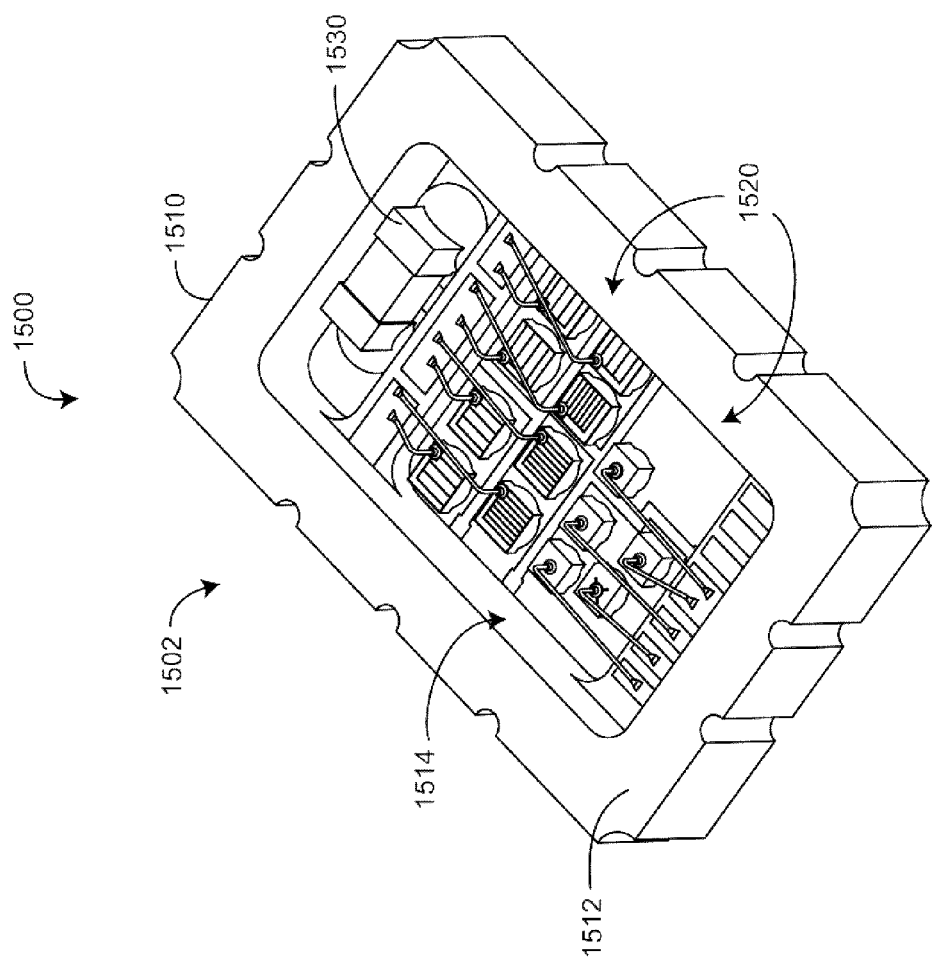

FIGS. 15A-B illustrate emitters 1500, including an eight-LED emitter 1501 particularly advantageously for $SpO_2$, HbCO and HbMet measurements and a thirteen-LED emitter 1502 particularly advantageously for total hemoglobin (Hbt) measurements in addition to $SpO_2$, HbCO and HbMet. Each emitter 1500 has a ceramic substrate 1510, light-emitting diodes (LEDs) 1520 and a thermistor 1530. The ceramic substrate 1510 has a body 1512 defining a cavity 1514. The cavity 1514 contains bonding pads that mount an array of LEDs 1520. The ceramic substrate 1510 also has multiple layers of traces, feed-thrus and solder pads so as to interconnect the LEDs 1520 in an electrical grid. The solder pads allow a monitor to electrically activate the LEDs 1520 via the flex circuit 1112 (FIGS. 11A-B), the connector 1010 (FIG. 10) and an attached patient cable 1000 (FIG. 10). The cavity 1514 also contains a thermistor 1530, the resistance of which can be measured in order to determine the bulk temperature of the LEDs 1520. The thermal characteristics of ceramic stabilize and normalize the bulk temperature of the substrate 1510 so that the thermistor measurement of bulk temperature allows an accurate determination of LED temperature and, hence, LED wavelengths.

As shown in FIGS. 15A-B, an LED array 1520 is connected within an electrical grid of n rows and m columns totaling n+m LED drive lines where n and m are integers greater than one. The electrical grid advantageously minimizes the number of drive lines required to activate the LEDs 1520 while preserving flexibility to selectively activate individual LEDs 1520 in any sequence and multiple LEDs 1520 simultaneously. The electrical grid also facilitates setting LED currents so as to control intensity at each LED wavelength, determining operating wavelengths and monitoring total grid current so as to limit power dissipation. The LED array 1520 is physically configured in rows, which facilitates clustering LEDs according to wavelength so as to minimize pathlength variations and which facilitates equalization of LED intensities. In an embodiment the LED array 1520 comprises up to sixteen LEDs configured in an electrical grid of four rows and four columns. Each of four row drive lines provide a common anode connection to four LEDs, and each of four column drive lines provide a common cathode connection to four LEDs. Thus, sixteen LEDs are advantageously driven with only eight wires, including four anode drive lines and four cathode drive lines. In an embodiment, an LED array is partially populated with eight LEDs having nominal wavelengths as shown in TABLE 1. In an embodiment, the LED array is partially populated with thirteen LEDs having nominal wavelengths as shown in TABLE 2. Advantageously, LED array and the corresponding LED wavelengths are adapted to measure total hemoglobin (Hbt) in addition to $SpO_2$, pulse rate, HbCO and HbMet, among other physiological parameters. In an embodiment, LEDs D1-D5 are encapsulated with an attenuating epoxy 1660 (FIGS. 16B, F) so as to equalize LED intensities. In an embodiment, a clear fill epoxy 1670 (FIGS. 16B, F) mixed with 1-20 μm microspheres is dispersed and cured over the LEDs. An LED array and corresponding drivers for an electrical grid are disclosed in U.S. patent application Ser. No. 11/367,013, filed Mar. 1, 2006, titled Multiple Wavelength Sensor Emitters, incorporated by reference herein.

TABLE 1

Nominal LED Wavelengths (in nm)

| LED | λ | Row | Col |
|-----|-----|-----|-----|
| D1  | 630 | 1 | 1 |
| D2  | 620 | 1 | 2 |
| D3  |     | 1 | 3 |
| D4  |     | 1 | 4 |
| D5  | 700 | 2 | 1 |
| D6  | 720 | 2 | 2 |
| D7  | 660 | 2 | 3 |
| D8  | 805 | 2 | 4 |
| D9  | 905 | 3 | 1 |
| D10 |     | 3 | 2 |
| D11 |     | 3 | 3 |
| D12 |     | 3 | 4 |
| D13 | 645 | 4 | 1 |
| D14 |     | 4 | 2 |
| D15 |     | 4 | 3 |
| D16 |     | 4 | 4 |

TABLE 2

Nominal LED Wavelengths (in nm)

| LED | λ | Row | Col |
|-----|------|-----|-----|
| D1  | 700  | 1 | 1 |
| D2  | 660  | 1 | 2 |
| D3  | 730  | 1 | 3 |
| D4  | 805  | 1 | 4 |
| D5  | 905  | 2 | 1 |
| D6  |      | 2 | 2 |
| D7  |      | 2 | 3 |
| D8  |      | 2 | 4 |
| D9  | 630  | 3 | 1 |
| D10 | 620  | 3 | 2 |
| D11 | 1170 | 3 | 3 |
| D12 | 1240 | 3 | 4 |
| D13 | 645  | 4 | 1 |
| D14 | 1270 | 4 | 2 |
| D15 | 1040 | 4 | 3 |
| D16 | 1270 | 4 | 4 |

FIGS. 16A-H further illustrate emitters 1500 having bonding pads 1610, mounting pads 1620, solder pads 1630, bonding wires 1640, an optical filter 1660 and an encapsulant 1670. The mounting pads 1620 mount and electrically connect a first side (anode or cathode) of the array of LEDs 1520 (FIGS. 15A-B) into an electrical grid. The bonding pads 1610 electrically connect a second side (cathode or anode) of the LEDs 1520 (FIGS. 15A-B) into the electrical grid, via bonding wires 1640. The thermistor 1530 is also attached to a pair of mounting pads 1620. Plated "feed-thru" holes electrically connect the mounting pads 1620 and the bonding pads 1610 on the ceramic substrate top side (FIGS. 16A, E) with solder pads 1630 on the bottom side (FIGS. 16D, H).

Figure 17A:
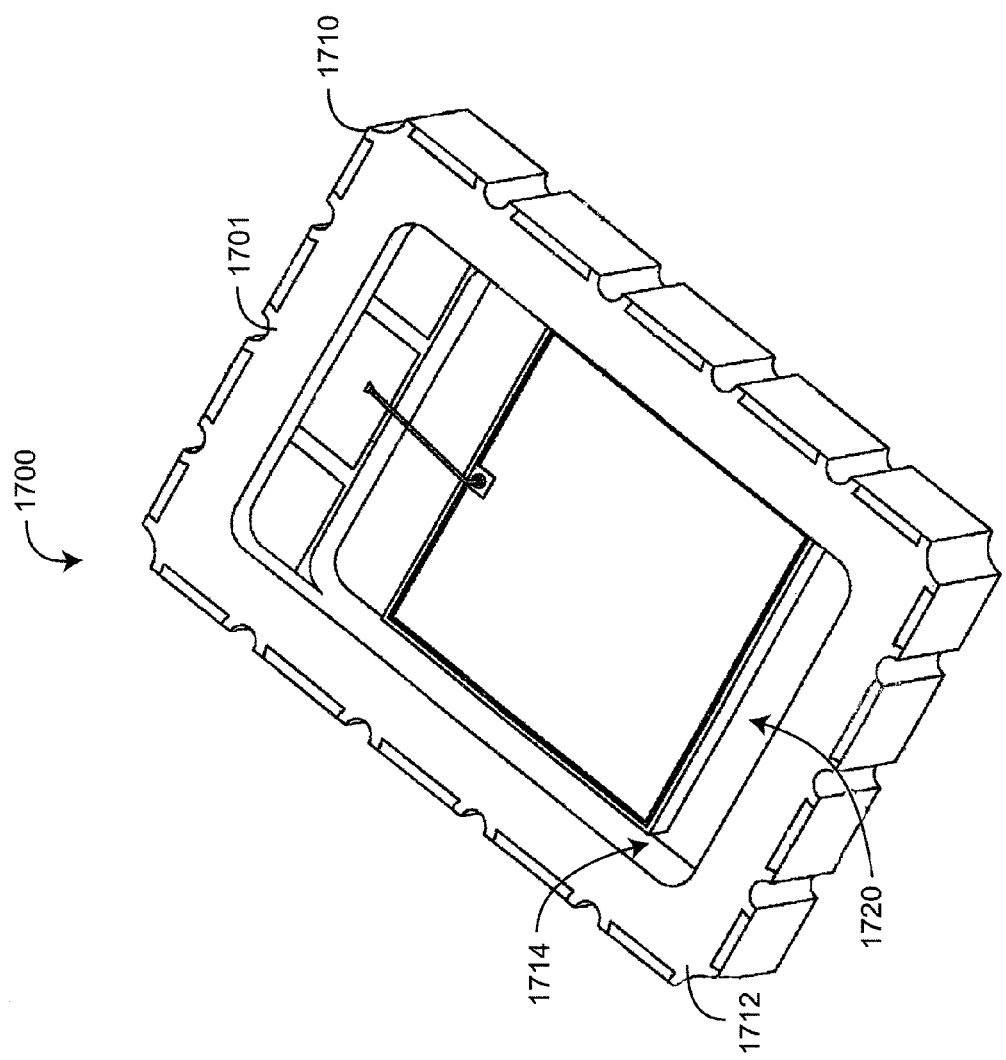
FIGS. 17A-B are perspective views of a detector components.
Figure 17B:
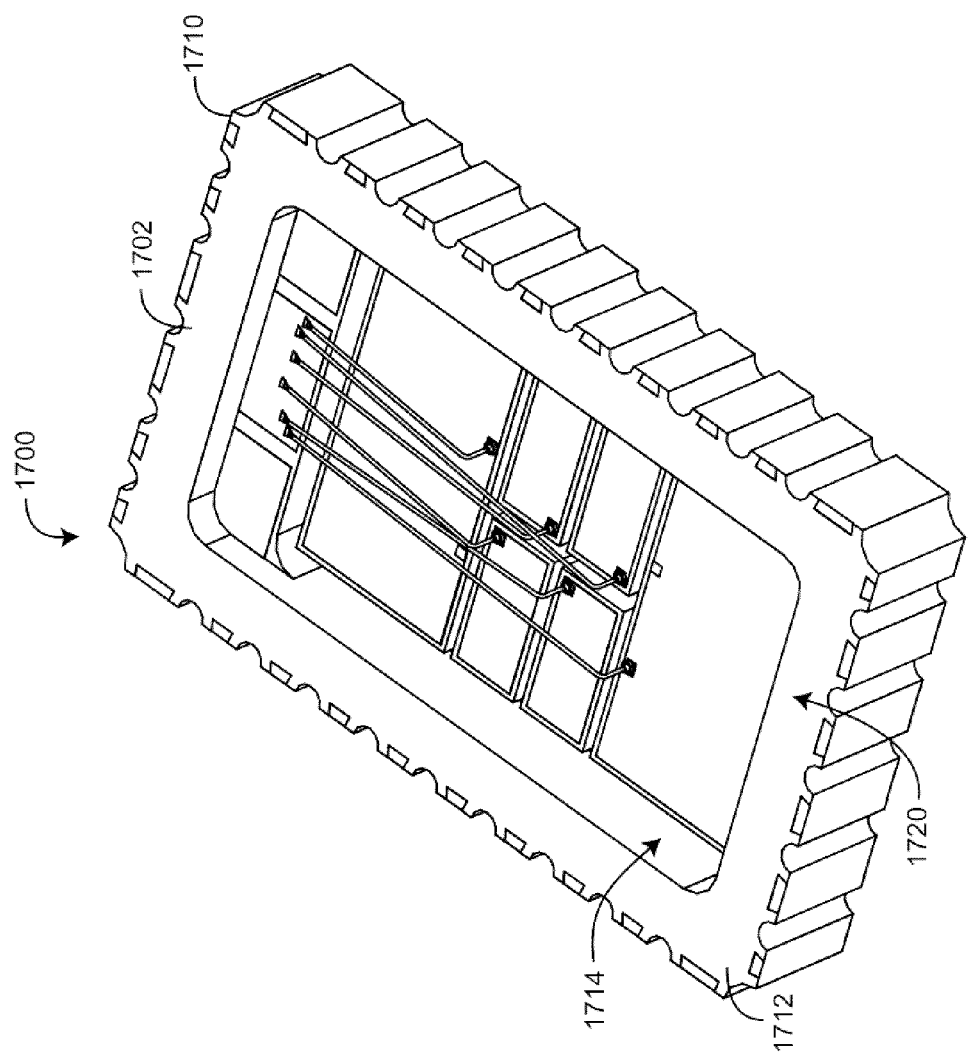

FIGS. 17A-B illustrate detectors 1700 including a detector 1701 utilizing a single Si photodiode 1720 particularly advantageous for $SpO_2$, HbCO and HbMet measurements and a detector 1702 utilizing multiple photodiodes 1720 particularly advantageous for total hemoglobin (Hbt) measurements in addition to $SpO_2$, HbCO and HbMet. Each detector 1700 has a ceramic substrate 1710 and one or more photodiodes 1720. The ceramic substrate 1710 has a body 1712 defining a cavity 1714. The cavity 1714 contains bonding pads that mount the photodiode(s) 1720 and electrically connect the photodiode(s) 1720, if more than one, in parallel. The solder pads (not visible) output detector current to a monitor via the flex circuit 1112 (FIGS. 11A-B), the connector 1010 (FIG. 10) and an attached patient cable 1000 (FIG. 10). In an embodiment, a single Si photodiode 1720 is utilized. In an embodiment, multiple photodiodes advantageously utilize parallel connected combinations of one or more Si photodiodes and one or more InGaAs photodiodes. The Si photodiodes are generally responsive to red and shorter near-IR wavelengths. The InGaAs photodiodes are generally responsive to longer near-IR wavelengths. Thus, the parallel combination of Si and InGaAs photodiodes extends the bandwidth of the detector component 1700 over the entire range of nominal LED emitter wavelengths, described above, so as to allow a corresponding monitor to non-invasively measure a patient's total hemoglobin (Hbt) among other blood parameters.

FIGS. 18A-H further illustrate a detector component 1700 having a ceramic substrate 1710, solder pads 1810, a mounting pad 1820, bonding pads 1830, wire bonds 1840, Si photodiodes 1860 and InGaAs photodiodes 1870. The photodiodes 1860, 1870 are mounted on a mounting pad 1820 electrically connected to a first solder pad 1810. The photodiodes 1860, 1870 are wire bonded 1840 to a bonding pad 1830 electrically connected to a second solder pad 1810. The solder pads 1810 include DET−, DET+ and GND pads that mount the detector component 1700/detector 1900 to a flex circuit 1210, as described with respect to FIGS. 12A-C, above. A clear epoxy 1880 fills the remainder of the detector cavity 1714 (FIGS. 17A-B).

Figure 19A:
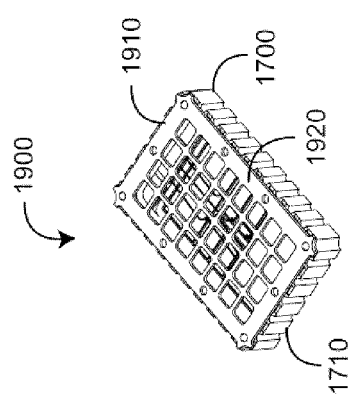
FIGS. 19A-B are perspective and top views, respectively, of a detector.
Figure 19B:
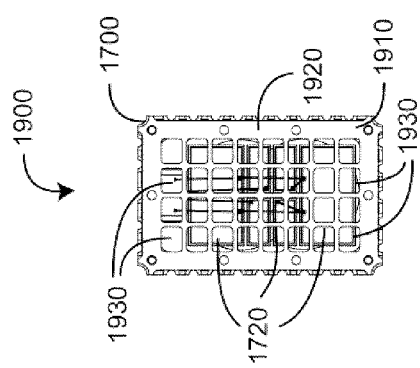

FIGS. 19A-B illustrate a detector 1900 having a detector component 1700 and a shield 1910. The shield 1910 has a conductive surface 1920 defining windows 1930. The windows 1930 can be any shape appropriate to the passage of light and the blocking of electromagnetic noise. In an embodiment, the windows 1930 are large rectangles with minimal interconnect so as to allow for a substantial passage of emitted light to the photodiodes 1720. In an embodiment, the shield 1910 is soldered to the ceramic substrate 1710 on at least the four corners, electrically and mechanically coupling the shield 1910 to the ceramic substrate 1710 and allowing the shield to form one side of a Faraday cage. Mechanical coupling can be, for example, gluing, welding, soldering, screwing, snap fitting, or other suitable fastening. Electrical coupling can be, for example, soldering, wire bonding, die bonding, or other suitable forms of electrical connection. In an embodiment, the ceramic substrate 1710 is printed with shielding material to complete the Faraday cage. Additional shielding material can be attached to or plated on the ceramic substrate 1710.

FIGS. 20A-B illustrate other photodiode array configures 2001, 2002. In an embodiment 2001, one or two relatively large surface area InGaAs photodiodes 2020 are mounted between two relatively large surface area Si photodiodes 2010. In an embodiment 2002, four relatively medium surface area photodiodes 2030, 2040 are arrayed so as to intersperse Si photodiodes 2030 and InGaAs photodiodes 2040. In other embodiments, various photodiodes of relatively small, medium and large surface areas and in various mixes of Si and InGaAs technologies are arranged in various topologies within the detector substrate cavity so as to advantageously measure total hemoglobin among other parameters. Other embodiments incorporate other photodiode technologies capable of measuring red and infrared wavelengths in addition to, or in lieu of, Si and InGaAs technologies.

Figure 21A:
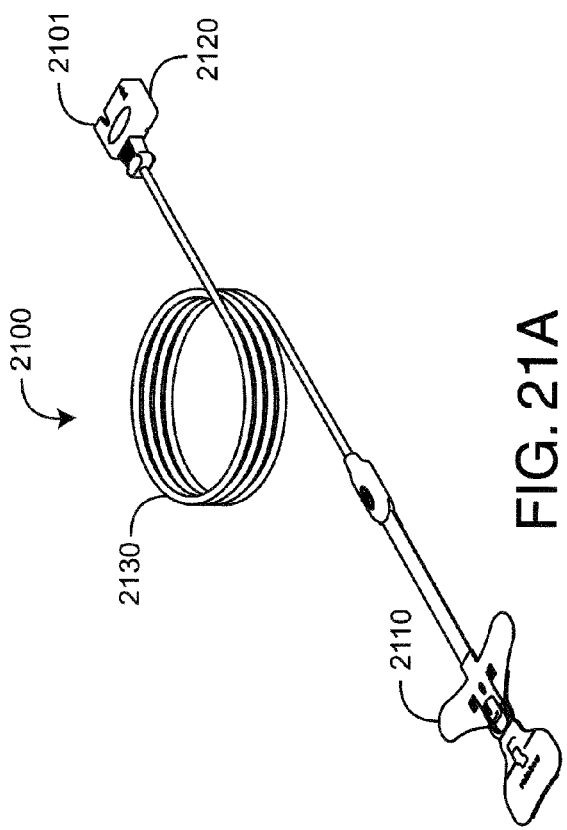
FIGS. 21A-B are perspective views of multiple wavelength optical sensor embodiments.
Figure 21B:
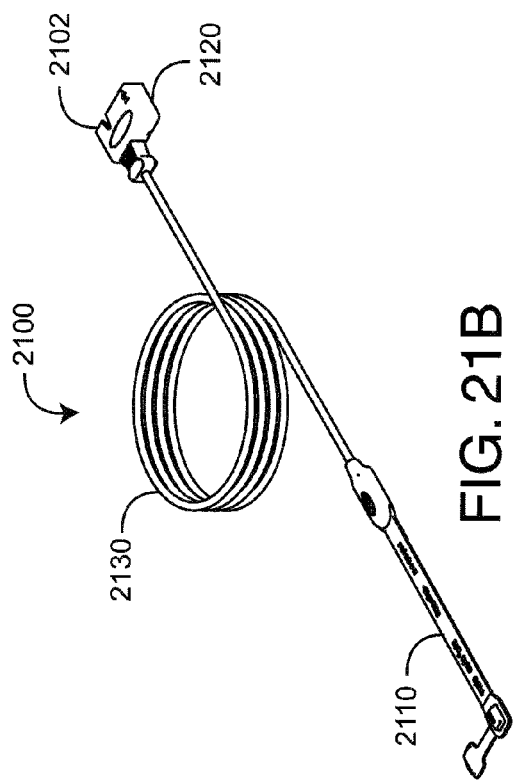

FIGS. 21A-B illustrate additional embodiments of a multiple wavelength optical sensor 2100. In particular, disposable sensors include an adult/pediatric sensor 2101 and an infant/pediatric sensor 2102. Each sensor 2100 has a tape end 2110 and an opposite connector end 2120 electrically and mechanically interconnected via a cable 2130. The tape end 2110 attaches an emitter and detector to a tissue site. An emitter, described below, emits transmits light into the tissue site and a detector, also described below, generates a sensor signal responsive to the emitted light after tissue absorption. The sensor signal is communicated via the cable 2130 to the connector 2120. The connector 2120 mates with a patient cable (not shown) that communicates the sensor signal to a monitor (not shown). The relative spacing between the emitter and detector are selected to obtain a desired alignment of the emitter and detector when the sensor is attached to the body tissue of a patient.

Figure 22:
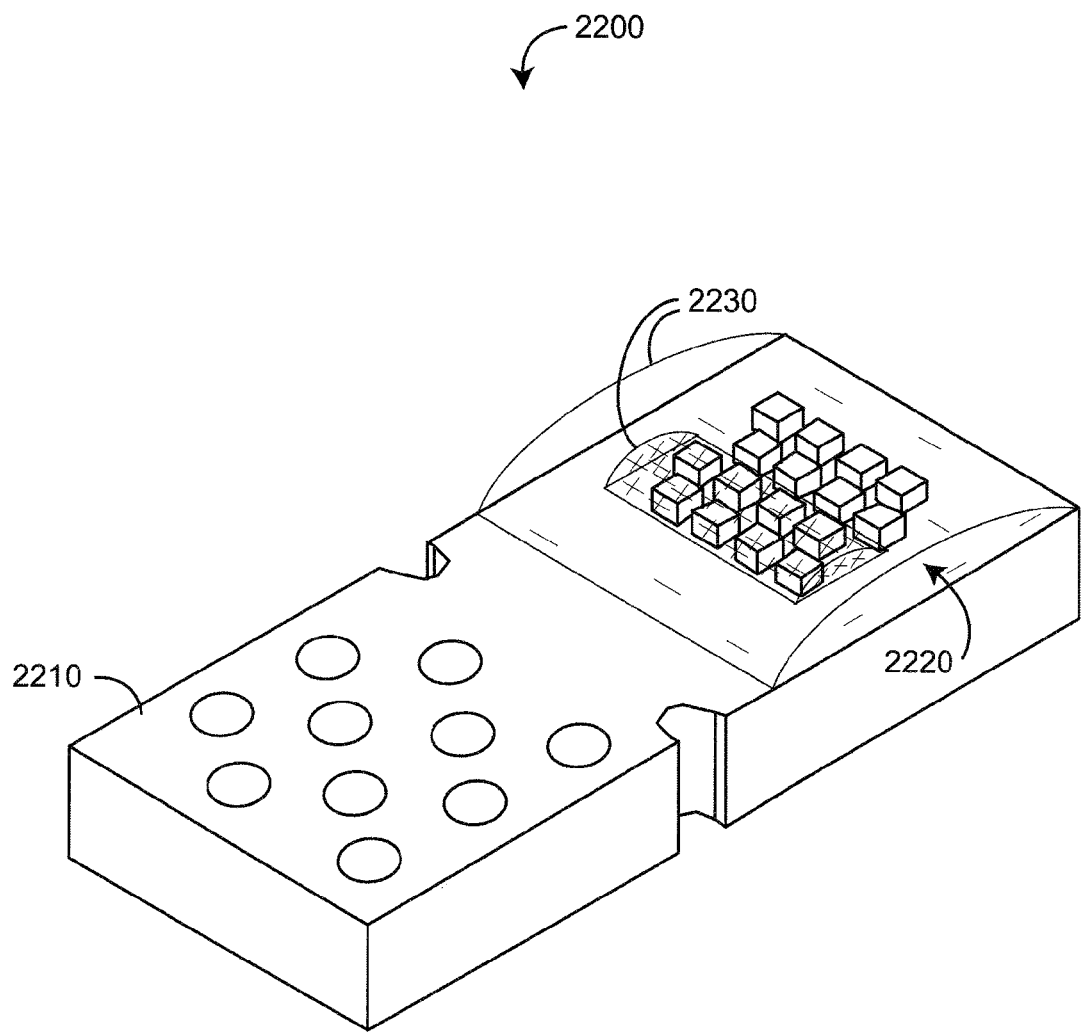
FIG. 22 is a perspective view of an emitter assembly.
Figures 24A, 24B, 24C, 24D:
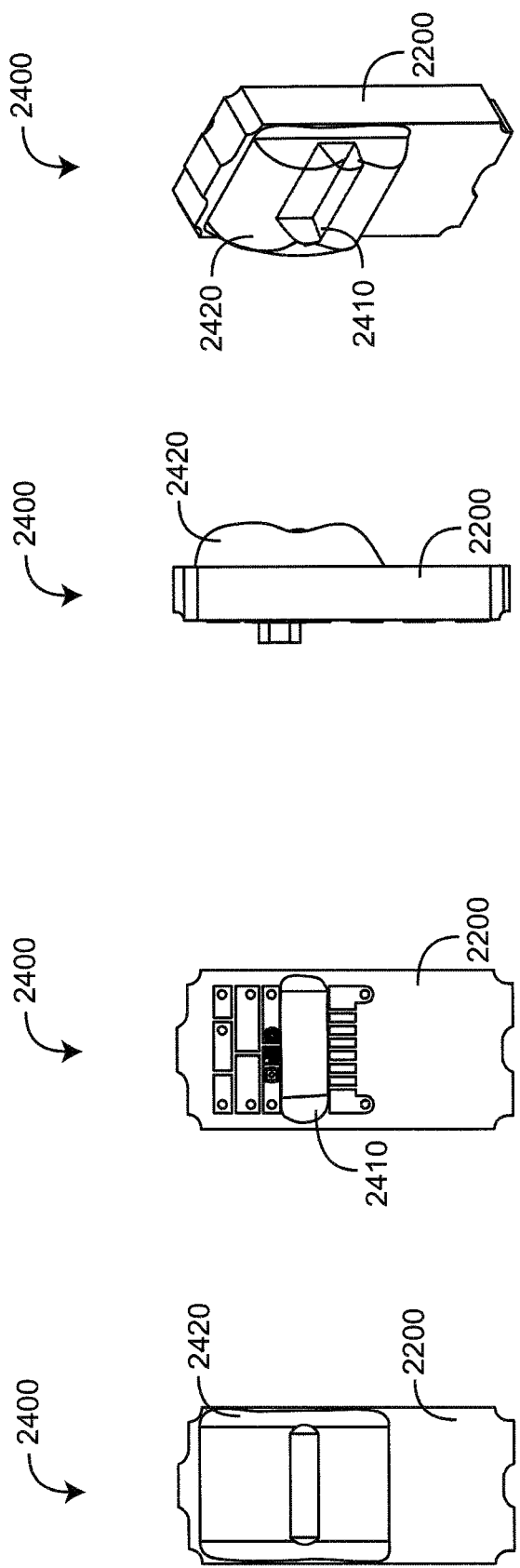
FIGS. 24A-D are views of an encapsulated emitter assembly.

FIG. 22 illustrates an emitter 2200 embodiment having a board substrate 2210, an LED array 2220 and one or more encapsulants 2230. The LED array 2220 emits optical radiation having multiple wavelengths of predetermined nominal values, advantageously allowing multiple parameter measurements. In particular, the LED array 2220 has multiple light emitting diodes (LEDs) that are physically arranged and electrically connected in an electrical grid to facilitate drive control, equalization, and minimization of optical pathlength differences at particular wavelengths. The LEDs are each activated by addressing at least one row and at least one column of the electrical grid, as described above. At least a portion of the encapsulants 2230 are advantageously configured to provide intensity equalization across a specific LED subset. In an embodiment, the LEDs emit light having wavelengths generally centered around the values shown in TABLE 3.

TABLE 3

Nominal LED Wavelengths

| LED | λ | Row | Col |
|-----|-----|-----|-----|
| D1 | 630 | 1 | 1 |
| D2 | 620 | 1 | 2 |
| D3 | 610 | 1 | 3 |
| D4 |  | 1 | 4 |
| D5 | 700 | 2 | 1 |
| D6 | 730 | 2 | 2 |
| D7 | 660 | 2 | 3 |
| D8 | 805 | 2 | 4 |
| D9 |  | 3 | 1 |
| D10 |  | 3 | 2 |
| D11 |  | 3 | 3 |
| D12 | 905 | 3 | 4 |
| D13 |  | 4 | 1 |
| D14 |  | 4 | 2 |
| D15 |  | 4 | 3 |
| D16 |  | 4 | 4 |

FIGS. 23A-D illustrate a component-populated board substrate 2300 having a board substrate 2200, a LED array 2220, a thermistor 2310, bonding pads 2320, component pads 2330 and solder pads 2340. The LED array 2220 is soldered to the component pads 2330, which are electrically connected to the solder pads 2340. Accordingly, the solder pads 2340 provide an electrical connection via a flex circuit, described below, between the LED array 2220 and a sensor drive (FIG. 28) located in a monitor (not shown). The thermistor 2310 provides a bulk temperature measurement of the LED array 2220 so as to better determine LED operating wavelengths. Either the N or P side of each LED die is electrically connected to the component pads 2330. The opposite P or N side of each LED die is electrically connected to the wire-bond pads 2320.

FIGS. 24A-D illustrate an encapsulated board substrate 2400 having board substrate 2200, a first encapsulant 2410 and a second encapsulant 2420. The first encapsulant is colored so as to provide an optical filter to equalize the intensities of a specific LED subset. This equalization accounts for differences in LED intensity across the multiple wavelengths so as to at least reduce wavelength-dependent variations in detected intensity. In a particular embodiment, the first encapsulant 2410 encapsulates the shorter wavelength LEDs.

Figure 25:
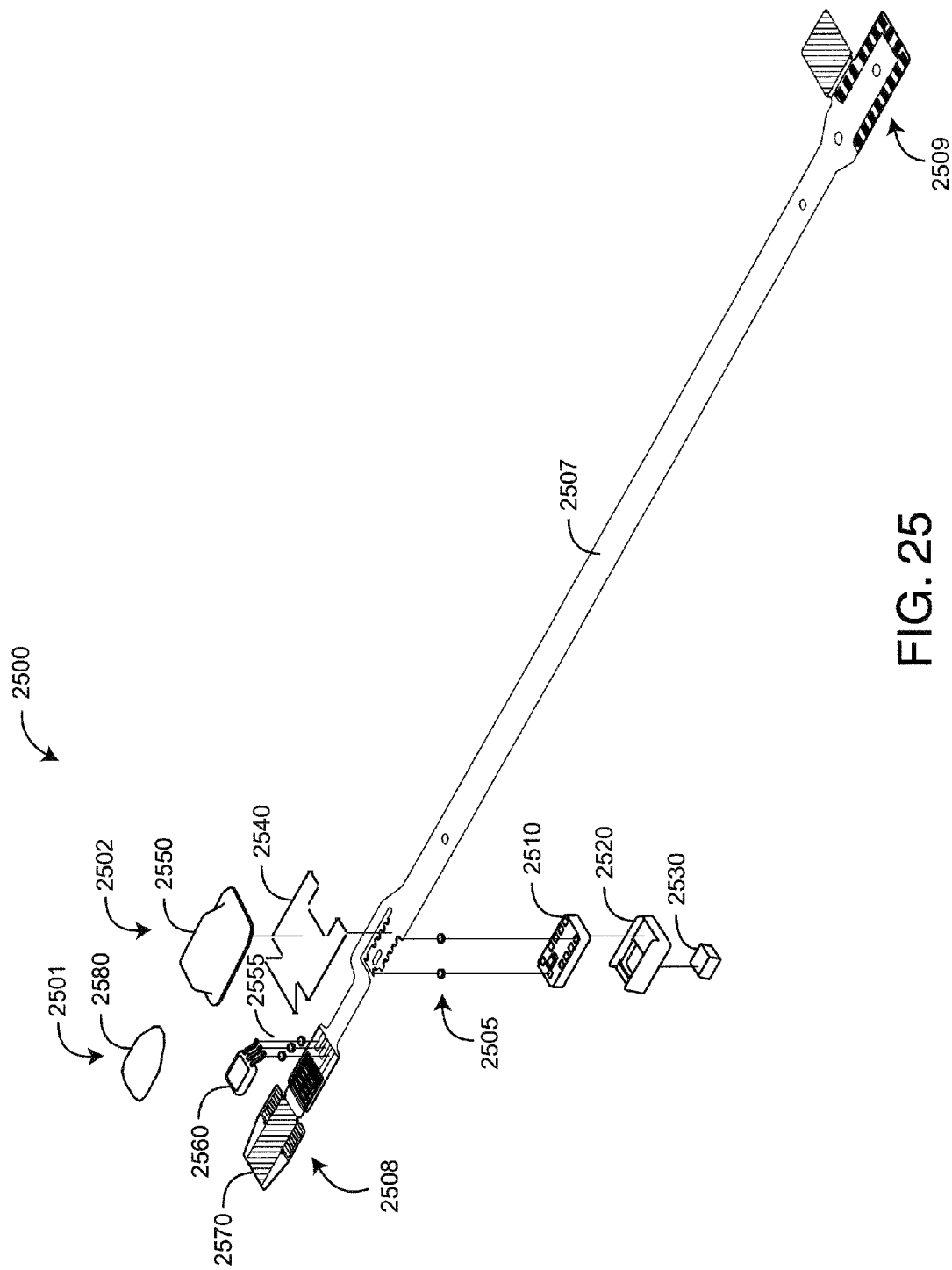
FIG. 25 is an exploded, perspective view of an optical assembly.

FIG. 25 illustrates a flex circuit assembly 2500 including a flex circuit 2507 having an optics end 2508 and a cable end 2509. FIGS. 26A-I describe a detector circuit assembly 2501 and an emitter circuit assembly 2502 at the optics end 2508. FIG. 27 describes a cable assembly at the cable end 2509. The emitter circuit assembly 2502 has an emitter 2510, a spacer 2520, an encapsulant 2530, a light barrier 2540 and an emitter cover 2550. The detector circuit assembly 2501 has a detector 2560, an EMI shield 2570 and a detector cover 2580. Solder 2505 attaches the emitter 2510 to flex circuit pads. Solder 2555 also attaches the detector 2560 to flex circuit pads. Advantageously, the spacer 2520 and encapsulant 2530 provide a relatively uniform illumination of patient tissue across all emitted wavelengths. In particular, the spacer 2520 provides a gap between the emitter LEDs and patient tissue, allowing the emitted light from each LED to spread as it propagates to a tissue site. In an embodiment, the gap is 70 mm. In an embodiment, the encapsulant is configured to diffuse or scatter emitter light from each LED as it propagates to a tissue site. In an embodiment, the encapsulant contains 0.1 mm glass beads, 25% by weight, in a clear silicon RTV. In an embodiment, the encapsulant contains filtering media that provides pass-band characteristics for the emitted wavelengths of the emitter assembly or notch filter characteristics away from the emitted wavelengths so as to substantially attenuate secondary emissions of the LEDs.

FIGS. 26A-I illustrate the detector circuit assembly 2501 and the emitter circuit assembly 2502. FIGS. 26A-E illustrates the detector assembly 2501 with an unfolded and folded EMI shield 2570. FIGS. 26F-I illustrate folding of a light barrier 2540 around the emitter 2510.

FIGS. 27A-E illustrate a cable assembly 2700. The sensor cable 2100 is mounted to a cable connector 2730 extending from the cable end 2509 of the flex circuit 2507. Detector wires 2770 are shielded at the flex circuit junction by a fold-over conductive ink flap 2740, which is connected to a cable inner shield 2750.

Figure 28:
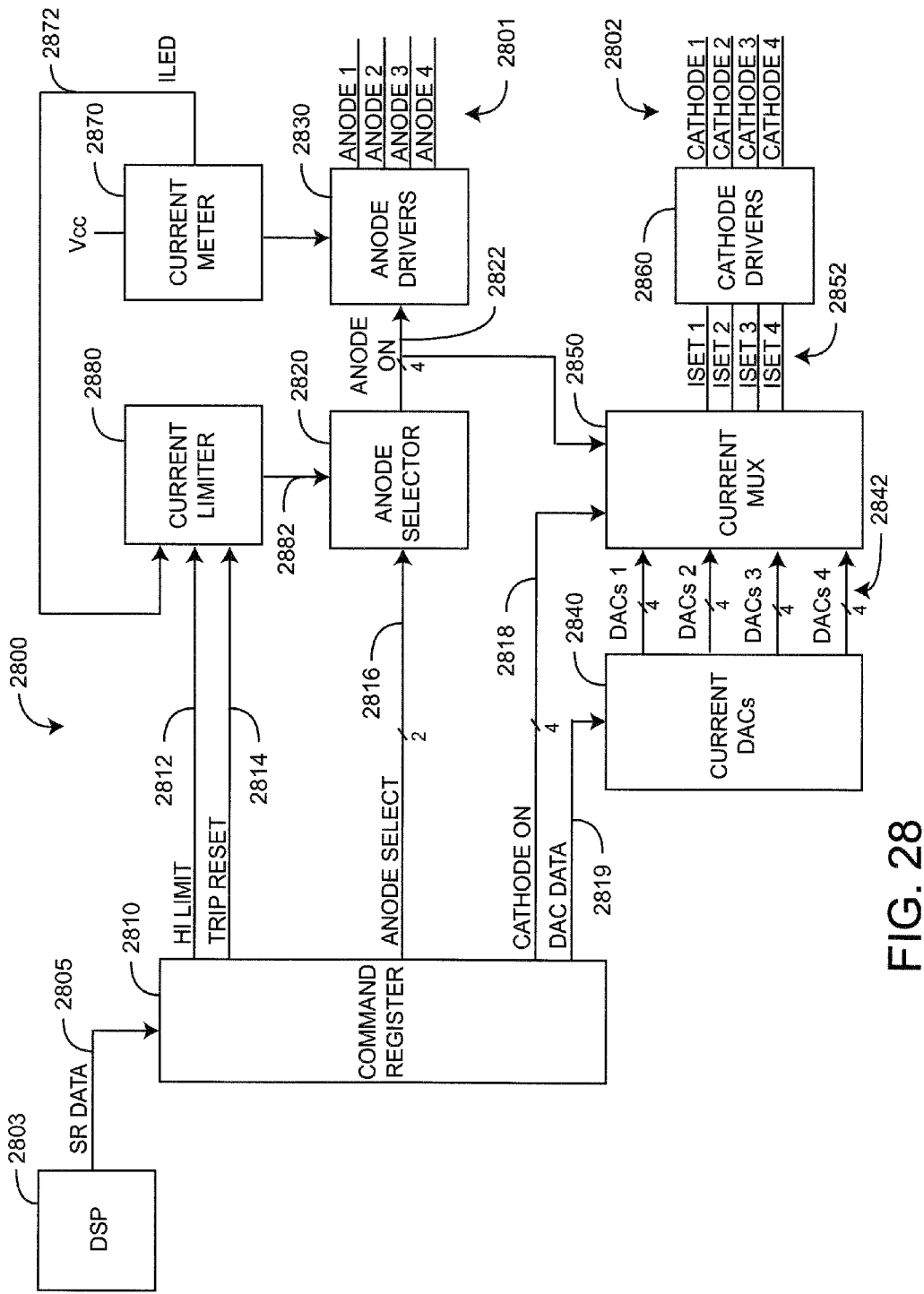
FIG. 28 is a general block diagram of an emitter driver.

FIG. 28 illustrates a sensor controller 2800 located in a monitor 100 (not shown) and configured to provide anode drive signals 2801 and cathode drive signals 2802 to an LED array. The DSP (digital signal processor) 2803, which performs signal processing functions for the monitor, also provides commands 2842 to the sensor controller 2800. These commands determine drive signal 2801, 2802 levels and timing. The sensor controller 2800 has a command register 2810, an anode selector 2820, anode drivers 2830, current DACs (digital-to-analog converters) 2840, a current multiplexer 2850, cathode drivers 2860, a current meter 2870 and a current limiter 2880. The command register 2810 provides control signals responsive to the DSP commands 2842. In one embodiment, the command register 2810 is a shift register that loads serial command data 2805 from the DSP 2803 and synchronously sets output bits that select or enable various functions within the sensor controller 2800, as described below.

As shown in FIG. 28, the anode selector 2820 is responsive to anode select 2816 inputs from the command register 2810 that determine which LED array row is active. Accordingly, the anode selector 2820 sets one of the anode on 2822 outputs to the anode drivers 2830, which pulls up to Vcc one of the anode outputs 2801 to the LED array.

Also shown in FIG. 28, the current DACs 2840 are responsive to command register data 2819 that determines the currents through each LEDr array column. In one embodiment, there are four, 12-bit DACs associated with each emitter array column, sixteen DACs in total. That is, there are four DAC outputs 2842 associated with each emitter array column corresponding to the currents associated with each row along that column. In a particular embodiment, all sixteen DACs 2840 are organized as a single shift register, and the command register 2810 serially clocks DAC data 2819 into the DACs 2840. A current multiplexer 2850 is responsive to cathode on 2818 inputs from the command register 2810 and anode on 2822 inputs from the anode selector 2820 so as to convert the appropriate DAC outputs 2842 to current set 2852 inputs to the cathode drivers 2860. The cathode drivers 2860 are responsive to the current set 2852 inputs to pull down to ground one to four of the cathode outputs 2802 to the LED array.

The current meter 2870 outputs a current measure 2872 that indicates the total LED current driving the LED array. The current limiter 2880 is responsive to the current measure 2872 and limits specified by the command register 2810 so as to prevent excessive power dissipation by the LED array. The current limiter 2880 provides an enable 2882 output to the anode selector 2820. A Hi Limit 2812 input specifies the higher of two preset current limits. The current limiter 2880 latches the enable 2882 output in an off condition when the current limit is exceeded, disabling the anode selector 2820. A trip reset 2814 input resets the enable 2882 output to re-enable the anode selector 2820.

A multiple wavelength sensor has been disclosed in detail in connection with various embodiments. These embodiments are disclosed by way of examples only and are not to limit the scope of the claims that follow. Although a multiple wavelength sensor has been disclosed with respect to various disposable sensor embodiments, other embodiments incorporate other tissue site attachment technologies including reusable and resposable sensors configured to attach to various tissue sites including fingers, hands, feet, toes, ears to name a few. Further, although a multiple wavelength sensor has been disclosed with respect to light transmission with respect to emitters, tissue site and detectors, other embodiments incorporate reflectance and transflectance configurations. A reusable sensor is disclosed in U.S. patent application Ser. No. 11/366,833, filed Mar. 1, 2006, titled Multiple Wavelength Sensor Attachment, incorporated by reference herein. One of ordinary skill in art will appreciate many variations and modifications.

What is claimed is:

1. A physiological sensor comprising:
an emitter that emits light having a plurality of wavelengths;
a detector that generates an output signal responsive to the emitted light after absorption by tissue, the detector comprising a plurality of Si photodiodes and at least one InGaAs photodiode connected in parallel;
an attachment assembly that removably attaches the emitter and the detector to tissue;
a spacer that provides a predetermined gap between the emitter and tissue when the emitter is attached to tissue; and
a light scattering medium disposed in an optical path between the emitter and tissue;
the spacer and the light scattering medium providing at least a substantially uniform illumination of tissue by the emitted light for at least one of the wavelengths,
wherein the at least one InGaAs photodiode is mounted interspersed with the plurality of Si photodiodes.

2. The physiological sensor according to claim 1 wherein the light scattering medium comprises glass beads mixed with an encapsulant disposed proximate the spacer.

3. The physiological sensor according to claim 2 wherein the light scattering medium further comprises microspheres mixed with an epoxy disposed proximate the emitter.

4. The physiological sensor according to claim 3 wherein the emitter comprises an array of at least eight light emitting diodes emitting light generally centered around eight unique wavelengths.

5. The physiological sensor according to claim 4 wherein the emitter comprises an array of at least thirteen light emitting diodes emitting light generally centered around at least twelve unique wavelengths.

6. The physiological sensor according to claim 1 wherein the detector comprises two Si photodiodes and four InGaAs photodiodes all connected in parallel.

7. The physiological sensor according to claim 4 wherein the light emitting diodes emit light within a first range of about 620-905 nm. and within a second range of about 1040-1270 nm.

8. The physiological sensor according to claim 1 wherein the detector includes at least two InGaAs photodiodes mounted between two Si photodiodes.

9. A physiological sensor comprising:
  an emitter configured to radiate light having a plurality of wavelengths into a tissue site;
  the emitter comprises a plurality of LEDs disposed within an emitter ceramic substrate;
  a detector configured to receive the light after absorption by pulsatile blood flow within the tissue site;
  the detector generates a sensor signal capable of being processed by a patient monitor so as to derive total hemoglobin (Hbt);
  the detector comprises a plurality of photodiodes disposed within a detector ceramic substrate; and
  a first set of the photodiodes is responsive to a first set of the wavelengths and a second set of the photodiodes is responsive to a second set of the wavelengths,
  wherein the plurality of photodiodes comprises a plurality of Si photodiodes and at least one InGaAs photodiode connected in parallel, and wherein the at least one InGaAs photodiode is mounted interspersed with the plurality of Si photodiodes.

10. The physiological sensor according to claim 9 further comprising a diffuser that scatters the radiated light so that a tissue site is uniformly illuminated across all of the wavelengths.

11. The physiological sensor according to claim 10 wherein the diffuser comprises at least one of:
  a first encapsulate containing glass beads mounted in a spacer proximate the emitter ceramic substrate; and
  a second encapsulate mixed with microspheres disposed on at least one of the plurality of LEDs within the emitter ceramic substrate.

12. The physiological sensor according to claim 9 wherein the LEDs radiate light generally centered around at least twelve unique wavelengths.

13. The physiological sensor according to claim 12 wherein the LEDs are mounted in an array of at least thirteen LEDs connected within an electrical grid.

14. The physiological sensor according to claim 13 wherein the twelve unique wavelengths comprise eight wavelengths within a first range of about 620-905 nm. and four wavelengths within a second range of about 1040-1270 nm.

15. The physiological sensor according to claim 9 wherein the detector includes at least two InGaAs photodiodes mounted between two Si photodiodes.

16. A physiological sensor comprising:
  a light source that radiates light having a plurality of wavelengths;
  a diffuser that scatters the radiated light so that a tissue site is uniformly illuminated across all of the wavelengths; and
  at least one detector that generates a sensor signal responsive to the radiated light after tissue attenuation, the at least one detector comprising a plurality of Si photodiodes and at least one InGaAs photodiode connected in parallel, wherein the at least one InGaAs photodiode is mounted interspersed with the plurality of Si photodiodes.

17. The physiological sensor according to claim 16 wherein the at least one detector includes at least two InGaAs photodiodes mounted between two Si photodiodes.

18. The physiological sensor according to claim 16 wherein the light source comprises:
  a ceramic substrate having conductors arranged as an electrical grid; and
  a plurality of LEDs mounted within the ceramic substrate in an array.

19. The physiological sensor according to claim 18 wherein the comprises:
  a first encapsulant having microspheres disposed over the LEDs; and
  a second encapsulant having glass beads disposed proximate the ceramic substrate.

20. The physiological sensor according to claim 19 further comprising a spacer disposed proximate the ceramic substrate so as to form a gap between the LEDs and the tissue site.

21. The physiological sensor according to claim 20 further comprising:
  a connector that connects to a patient cable so as to communicate the sensor signal to a monitor;
  a flexible coupling having an optical end proximate the light source and the detector and a connector end proximate the connector; and
  the flexible coupling having conductors that communicate the sensor signal from the optical end to the connector end.

* * * * *